(12) United States Patent
Kawano et al.

(10) Patent No.: US 7,918,786 B2
(45) Date of Patent: Apr. 5, 2011

(54) CAPSULE TYPE MEDICAL DEVICE SYSTEM, AND CAPSULE TYPE MEDICAL DEVICE

(75) Inventors: Hironao Kawano, Tokyo (JP); Hironobu Takizawa, Tokyo (JP); Takeshi Yokoi, Tokyo (JP); Masatoshi Homan, Tokyo (JP); Akio Uchiyama, Yokohama (JP)

(73) Assignee: Olympus Corporation, Tokyo (JP)

( * ) Notice: Subject to any disclaimer, the term of this patent is extended or adjusted under 35 U.S.C. 154(b) by 1208 days.

(21) Appl. No.: 10/984,279

(22) Filed: Nov. 9, 2004

(65) Prior Publication Data

US 2005/0183733 A1  Aug. 25, 2005

(30) Foreign Application Priority Data

Nov. 11, 2003 (JP) ................. 2003-381202
Dec. 25, 2003 (JP) ................. 2003-431118
Dec. 26, 2003 (JP) ................. 2003-432674

(51) Int. Cl.
*A61B 1/00* (2006.01)
*A61B 1/04* (2006.01)

(52) U.S. Cl. ...................... 600/117; 600/118

(58) Field of Classification Search .......... 600/103–104, 600/116–118
See application file for complete search history.

(56) References Cited

U.S. PATENT DOCUMENTS

| | | | |
|---|---|---|---|
| 4,784,133 A * | 11/1988 | Mackin .............................. 606/7 |
| 4,961,738 A * | 10/1990 | Mackin ............................ 606/15 |
| 6,175,764 B1 | 1/2001 | Loeb et al. |
| 6,181,965 B1 | 1/2001 | Loeb et al. |
| 6,453,199 B1 | 9/2002 | Kobozev |
| 6,709,388 B1 * | 3/2004 | Mosse et al. ................... 600/114 |
| 6,740,082 B2 * | 5/2004 | Shadduck ........................ 606/41 |
| 7,122,001 B2 | 10/2006 | Uchiyama et al. |
| 2001/0051766 A1 * | 12/2001 | Gazdzinski ................... 600/309 |
| 2002/0198439 A1 | 12/2002 | Mizuno |
| 2002/0198470 A1 | 12/2002 | Imran et al. |
| 2003/0020810 A1 | 1/2003 | Takizawa et al. |
| 2003/0060734 A1 * | 3/2003 | Yokoi et al. ................... 600/593 |
| 2003/0073935 A1 | 4/2003 | Segawa et al. |
| 2003/0093088 A1 | 5/2003 | Long et al. |
| 2003/0125788 A1 | 7/2003 | Long |

(Continued)

FOREIGN PATENT DOCUMENTS

JP  2003-038424  2/2003

(Continued)

OTHER PUBLICATIONS

Supplementary European Search Report dated Sep. 18, 2009.

*Primary Examiner* — Philip R Smith
(74) *Attorney, Agent, or Firm* — Scully, Scott, Murphy & Presser, P.C.

(57) ABSTRACT

This capsule type medical device system includes: a position detection device 4 which detects the position within the living body of a capsule type medical device 2 which can be ingested to within the living body; an electrode 5 which is provided in the vicinity of the outer surface of the capsule type medical device 2, and which applies an electrical stimulus to living body tissue; and a control device 6 which controls the electric current which flows to the electrode 5; and the control device 6 controls the electric current which flows to the electrode 5 based upon positional information which is detected by the position detection device 4.

28 Claims, 20 Drawing Sheets

U.S. PATENT DOCUMENTS

| | | |
|---|---|---|
| 2003/0153866 A1 | 8/2003 | Long et al. |
| 2003/0208107 A1* | 11/2003 | Refael .......................... 600/300 |

FOREIGN PATENT DOCUMENTS

| | | |
|---|---|---|
| JP | 2003-070728 | 3/2003 |
| JP | 2003-093367 | 4/2003 |
| JP | 2003-144385 | 5/2003 |
| JP | 2003-299612 | 10/2003 |
| JP | 2003-299613 | 10/2003 |
| WO | WO 97/36646 | 10/1997 |
| WO | WO 01/08548 A1 | 2/2001 |
| WO | WO 01/87377 A2 | 11/2001 |

* cited by examiner

CAPSULE TYPE MEDICAL DEVICE SYSTEM, AND CAPSULE TYPE MEDICAL DEVICE

BACKGROUND OF THE INVENTION

1. Field of the Invention

The present invention relates to a capsule type medical device system which observes the inside of a living body, and in particular, which shifts within the body while applying electrical stimuli to living body tissues, and which is capable of observing a desired site.

The present application claims the priority of Japanese Patent Application 2003-432674 filed upon Dec. 26, 2003, Japanese Patent Application 2003-381202 filed upon Nov. 11, 2003, and Japanese Patent Application 2003-431118 filed upon Dec. 25, 2003, and incorporates the contents thereof herein by reference.

2. Description of Related Art

As methods by which a person who is to be investigated may check the state of his own health, for example, from the past, there have been generally known methods for performing various types of checks by human examination or by endoscopy or the like. Furthermore, there is a known method of investigation with a capsule type medical device, in which a testing module which is formed as a capsule is swallowed and is ingested to within the living body, so that his state of health can easily be checked. There have been various sorts of proposal for this kind of capsule type medical device, and, as one thereof, there is, for example, a known type of capsule type medical device of an electrically propelled type, which shifts within the living body by applying a local electrical stimulus via an electrode to living body tissue, thus taking advantage of the shrinking action of such electrical stimulation upon living body tissue (for example, refer to International Publication No. WO 01/08548).

Normally, when such a capsule type medical device is ingested to within the living body, it shifts naturally along his alimentary canal due to the peristaltic movement within, for example, his small intestine, by contrast, by applying local electrical stimuli to the living body tissue, this type of electrically propelled capsule type medical device is able, by performing shrinkage operation upon the living body tissue which is different from the peristaltic movement, to encourage its shifting along the direction of progress, or to perform shifting in the opposite direction to the direction of progress. Therefore, it is possible to perform observations with high efficiency, since it is possible to perform detailed observation by arriving quickly at the desired site for observation, and by lingering for some time at the same position.

SUMMARY OF THE INVENTION

The present invention proposes a capsule type medical device system which includes a capsule type medical device which can be ingested to, within the living body, further including: a position detection device which detects the position of the capsule type medical device within the living body; an electrode which is provided in the vicinity of the outer surface of the capsule type medical device, and which applies an electrical stimulus to living body tissue; and a control device which controls the electric current which flows to the electrode; wherein the control device controls the electric current which flows to the electrode, based upon positional information which is detected by the position detection device.

With the capsule type medical device system of the present invention, it is preferable that the capsule type medical device includes an acquisition device which acquires in-vivo information, and the position detection device decides upon the position of the capsule type medical device within the living body, by using the in-vivo information which is acquired by the acquisition device.

With the capsule type medical device system of the present invention, it is preferable that the capsule type medical device system further includes an external device which is disposed external to the living body, wherein a transmission section which transmits a physical quantity is provided to at least one or the other of the capsule type medical device and the external device, a detection section which detects the physical quantity which is transmitted from the transmission section is provided to the other, and the position detection device detects the position of the capsule type medical device within the living body, by using the physical quantity which is detected by the detection section.

With the capsule type medical device system of the present invention, it is preferable that the capsule type medical device system further includes an external device which is disposed outside the living body, wherein the capsule type medical device includes an internal acceleration sensor, the external device includes an external acceleration sensor, and the position detection device detects the position of the capsule type medical device within the living body, based upon the difference between the value detected by the internal acceleration sensor, and the value detected by the external acceleration sensor.

With the capsule type medical device system of the present invention, it is preferable that the position detection device includes a setting section in which a necessary parameter until the capsule type medical device arrives at a target site within the living body is set in advance.

With the capsule type medical device system of the present invention, it is preferable that the capsule type medical device includes a balloon which can be expanded so as to closely contact to living body tissue, or can be shrunk down, the electrode is provided upon the outer surface of the balloon, and the control device expands or shrinks down the balloon, based upon the positional information.

With the capsule type medical device system of the present invention, it is preferable that the electrode is provided in plurality, and the control device controls the electric current which flows in the plurality of electrodes, based upon the positional information.

The present invention proposes a capsule type medical device, including: a capsule shaped casing which can be ingested to within the living body; an electrical stimulation device which includes a plurality of electrodes which are used for applying electrical stimuli to living body tissue; an electrode selection device which selects an electrode from among the plurality of electrodes, to apply an electrical stimulus; a contact detection device which electrically detects the electrode which is in contact with the living body tissue; and a control section which controls the various devices.

With the capsule type medical device of the present invention, it is preferable that the capsule type medical device further including: an acquisition device which acquires in-vivo information; and a storage device which stores the in-vivo information.

With the capsule type medical device of the present invention, it is preferable that the electrical stimulation device includes: a waveform generator which generates a predetermined voltage waveform; a conversion circuit which converts the voltage waveform to electric current; a limitation circuit which is used for adjusting the electric current which flows to the electrode; and an electric current sensor which detects the electric current, the control section adjusts the gain of the limitation circuit according to the output of the electric current sensor.

With the capsule type medical device of the present invention, it is preferable that the contact detection device is a force detection device.

With the capsule type medical device of the present invention, it is preferable that the contact detection device measures the impedance between the electrode which is connected to the high electrical potential side and the electrode which is connected to the low electrical potential side.

With the capsule type medical device of the present invention, it is preferable that the capsule type medical device further includes a sensor which detects shifting of the casing based upon the acceleration or the speed when the casing shifts.

The present invention proposes a capsule type medical device system, including: a capsule type medical device which can be ingested to within the living body; and an external device which is disposed external to the living body; wherein the capsule type medical device includes: a capsule shaped casing; an acquisition device which acquires in-vivo information; a storage device which accumulates the in-vivo information; an internal communication device which transmits and receives information with the external device; an electrical stimulation device which includes a plurality of electrodes which are used for applying electrical stimulation to living body tissue; a contact detection device which electrically detects that the electrodes are contacting the living body tissue, and which is used for selecting electrodes from the plurality of electrodes for applying electrical stimulation; and a control section which controls the various devices; the external device includes: an external communication device which transmits and receives information with the capsule type medical device; a recording device which accumulates the in-vivo information; and an external control section which controls the various devices.

The present invention proposes a capsule type medical device, including: a capsule shaped casing; an imaging device which takes images of the inside of the living body; an electrical stimulation device which is provided upon the outer surface of the casing, and which includes an electrode which applies an electrical stimulus to living body tissue; and a control section which operates the imaging device and the electrical stimulation device each at its own different timing.

The present invention proposes a capsule type medical device, including: a capsule shaped casing; an imaging device which takes images of the inside of the living body; an electrical stimulation device which are provided upon the outer surface of one end and of the other end of the casing with respect to its axial direction, and which includes electrodes which apply an electrical stimulus to living body tissue; and a control section which operates the imaging device and the electrical stimulation device at the same time.

The present invention proposes a capsule type medical device, including: a capsule shaped casing; an imaging device which takes images of the inside of the living body; an electrical stimulation device which is provided upon the outer surface of the casing and which includes an electrode which applies an electrical stimulus to living body tissue; and a control section which operates the imaging device after a predetermined time period has elapsed, after having operated the electrical stimulation device.

With the capsule type medical device system of the present invention, it is preferable that the capsule type medical device system further including: an acquisition device which acquires in-vivo information; and a storage device which stores the in-vivo information.

With the capsule type medical device system of the present invention, it is preferable that the capsule type medical device system further including: the electrical stimulation device which includes a plurality of the electrodes; an electrode selection device which selects an electrode from among the plurality of electrodes, to apply an electrical stimulus; a contact detection device which electrically detects that the electrode is in contact with the living body tissue; and a control section which controls the various devices.

With the capsule type medical device system of the present invention, it is preferable that the electrical stimulation device includes: a waveform generator which generates a predetermined voltage waveform; a conversion circuit which converts the voltage waveform to electric current; a limitation circuit which is used for adjusting the electric current which flows to the electrode; and an electric current sensor which detects the electric current, the control section adjusts the gain of the limitation circuit according to the output of the electric current sensor.

With the capsule type medical device system of the present invention, it is preferable that the position of the capsule type medical device is detected by pattern recognition of the shift path of the capsule type medical device which is acquired by the position detection device.

With the capsule type medical device system of the present invention, it is preferable that the capsule type medical device system further comprising an external device which is disposed externally to the living body, wherein the capsule type medical device includes an internal speed sensor, the external device includes an external speed sensor, and the position detection device detects the position of the capsule type medical device within the living body, based upon the difference between the value detected by the internal speed sensor, and the value detected by the external speed sensor.

PREFERRED EMBODIMENTS FOR IMPLEMENTING THE INVENTION

In the following, the first embodiment of the capsule type medical device system of the present invention will be explained with reference to FIG. 1 through FIG 5.

Figure 1:
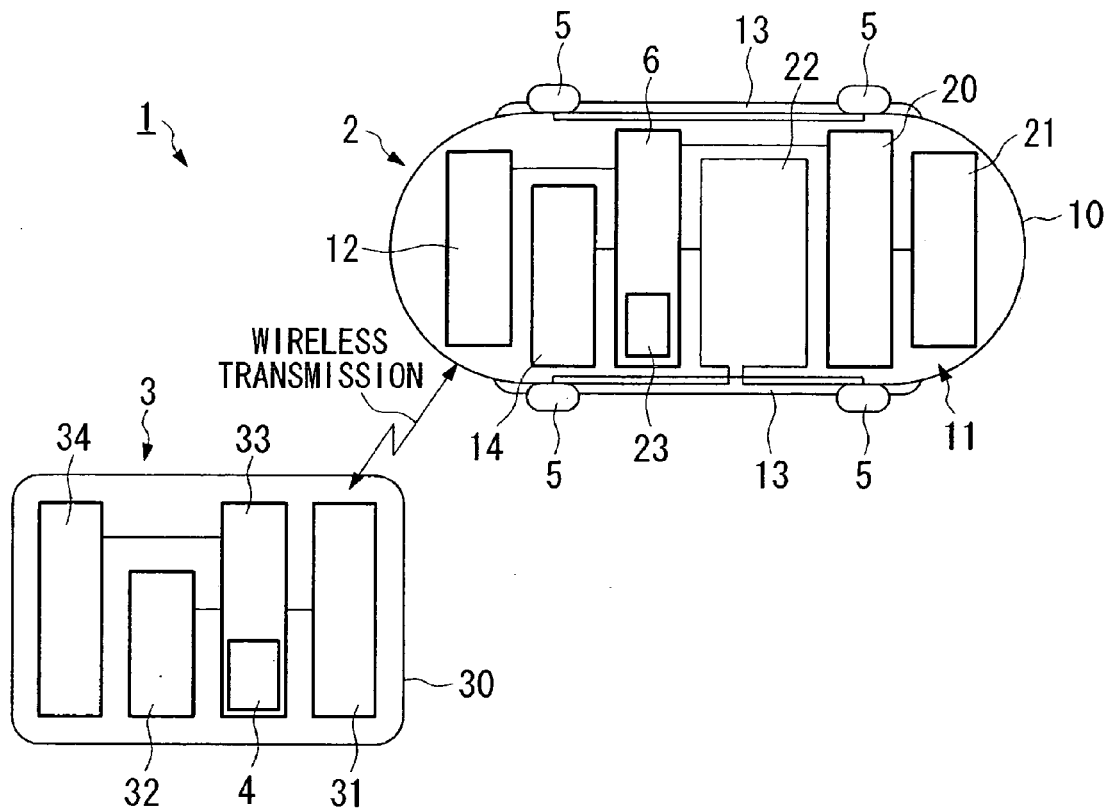
FIG. 1 is a structural diagram showing a first embodiment of the capsule type medical device system according to the present invention.

As shown in FIG. 1, the capsule type medical device system 1 of this embodiment includes a capsule type medical device 2 which can be ingested to within the living body (to within a living body), an external device 3 which is disposed outside the living body, a position detection circuit (position detection device) 4 which detects the position of the capsule type medical device 2 within the living body, electrodes 5 which are provided in the vicinity of the outer surface of the capsule type medical device 2 and which apply a stimulus to living body tissue, and a control section (a control device) 6 which controls the electric current which flows to the electrodes 5.

This capsule type medical device 2 includes: a capsule shaped casing 10; an acquisition device (an imaging device) 11 which acquires in-vivo information by taking images of the interior of his body; a wireless transmission and reception section (a transmission section, a detection section) 12 which, by generating and receiving radio waves (physical quantities), send and receive information signals to and from the external device 3; a balloon 13 which can be expanded so as to closely contact to living body tissue, and which can be shrunk; and a battery 14 which supplies electrical power to these various structural elements.

The casing 10 is made from a plastic or the like so as to enclose its interior, and a transparent cover not shown in the figures is provided over one of its ends. An imaging element 20 which obtains an image by taking images various parts of the inside of the living body, and an optical system 21 such as a LED or the like which illuminates the visual range of this imaging element 20 by irradiating it with illumination light are provided at the interior of this transparent cover. In other words, this imaging element 20 and optical system 21 constitute an acquisition device 11.

Furthermore, the above described balloon 13 is fitted around the periphery of the casing 10, so as to enwrap the casing 10. This balloon 13 is made from an elastic substance such as rubber or the like which can expand and contract, and, by an expansion and shrinkage mechanism 22 which is provided within the casing 10, as for example shown in FIG. 2, it is possible to supply a flow of air or the like to within this balloon 13 and thereby to expand it, or to shrink the balloon 13 by sucking out a mass of air from within the balloon 13. It should be understood that this expansion and shrinkage mechanism 22 is controlled by the control section 6. Furthermore, as shown in FIG. 1, when it has been shrunk, the balloon 13 adheres closely to the outer surface of the casing 10.

The electrodes 5 are provided upon the outer surface of the balloon 13. In other words, the electrodes 5 are positioned upon the outer surface of the casing 10 when the balloon 13 is shrunk down. Furthermore, the electrodes 5 are provided in a plurality upon the outer surface of the balloon 13, so as to be respectively disposed at the one end thereof and at the other end thereof with respect to the axial direction of the casing 10. It should be understood that, in this embodiment, electrodes 5 at the one end are positioned at the side of the imaging element 20. Furthermore, the electrodes 5 can apply an electrical stimulus by flowing an electric current (an electrical signal) which has been supplied from a current generation circuit 23 which is included in the control section 6 into the living body tissue. At this time, the control section 6 controls the electric current which flows to each of the electrodes 5 from the current generation circuit 23, based upon positional information from the external device 3. This will be explained in detail hereinafter.

The wireless transmission and reception section 12 includes a transmission and reception section main body which is not shown in the figures, and a signal transmission and reception antenna (a transmission antenna, a reception antenna) which transmits and receives radio wave signals; and it is able to transmit the above described in-vivo information, in other words the images which have been taken images by the imaging element 20, wirelessly to the external device 3. Furthermore, this wireless transmission and reception section 12 receives control signals (information) which will be described hereinafter which are transmitted wirelessly from the external device 3, and transmits them to the control section 6.

The control section 6 is equipped with the functions of, based upon the control signals which it has received from the wireless transmission and reception section 12, supplying electric current to the electrodes 5 from the current generation circuit 23, and stopping this supply of electric current to the electrodes 5 from the current generation circuit 23. Furthermore, the control section 6 is equipped with the function of controlling the expansion and shrinkage mechanism 22 based upon control signals, so as to operate the balloon 13 (i.e. to expand it or to shrink it). This action of the control section 6 will be explained hereinafter in detail. It should be understood that the control section 6 is equipped with the function of controlling the various structural elements described above in a combined manner.

As shown in FIG. 1, the external device 3 includes a main body 30, a wireless transmission and reception section (a transmission section, a detection section) 31 which performs signal transmission and receipt of information between itself and the capsule type medical device 2, a recording device 32 such as a memory or the like which accumulates the above described in-vivo information, in other words images, a control section 33 which controls these various structural elements, and a battery 34 which supplies electrical power to these various structural elements.

The main body 20 is made in the shape of a box from a metallic material such as aluminum or the like, or a plastic material or the like, and can be put on to his own body by the person who is the subject of investigation via a belt or the like. Therefore, the main body 20 is always arranged upon the outside of the body of the person who is the subject of investigation.

The wireless transmission and reception section 31, in the same manner as the wireless transmission and reception section 12 of the capsule type medical device 2, includes a transmission and reception section main body not shown in the figures and a signal transmission and reception antenna (a transmission antenna, a reception antenna) which transmits and receives radio wave signals; and, along with being equipped with the function of receiving the images, which are in-vivo information, which have been sent from the capsule type medical device 2 and have arrived, it is also equipped with the function of sending them to the control section 33.

The control section 33, after having performed predetermined processing upon images such as image processing and the like, records them as required in the recording device 34. Furthermore, a position detection circuit 4 is provided to the control circuit 33. For example, an image which is set in advance (a standard image) is set in this position detection circuit 4, and the position of the capsule type medical device 2 within the living body is detected by comparing together this set image and the image which has been sent and has arrived. It should be understood that, although this position detection circuit 4 detects the position of the capsule type medical device 2 by comparing together the image and the set image, this should not be considered to be limitative; it would also be acceptable to arrange to detect the position of the capsule type medical device 2 based upon the characteristic amount of a specific color in the image, or upon shapes or the like.

Furthermore, the control section 33 is equipped with the function of sending a control signal to the capsule type medical device 2 via the wireless transmission and reception section 31, according to the site within the living body (for example, the stomach, the small intestine, or the colon) at which it has been detected by the position detection circuit 4 that the capsule type medical device 2 is positioned.

It should be understood that, in this embodiment, the control section 33 is set so as to transmit, respectively: a control signal to apply an electrical stimulus, when the capsule type medical device 2 has arrived at the small intestine; a control signal to cause the balloon 13 to expand when it has arrived at the colon; and a control signal to cause the balloon 13 to shrink, along with stopping the electrical stimulation, when it has arrived at the anus. Moreover, it should be understood that the control signals which correspond to these sites within the living body are not limited to being the above described ones; it is possible to set them freely.

The case of observing the interior of the body of a person who is the subject of investigation with the capsule type medical device system 1 having the above described structure will now be explained.

Figure 3:
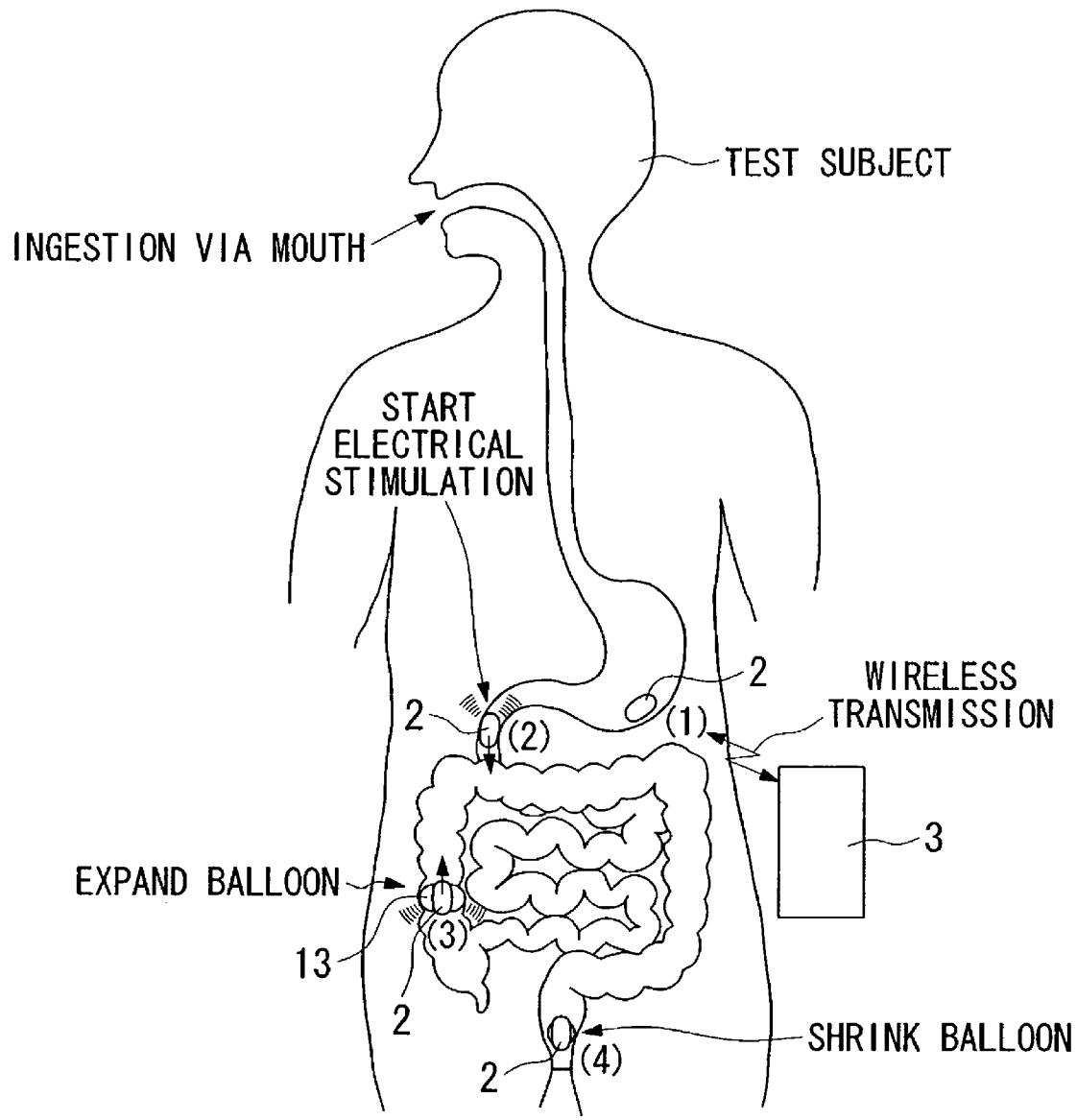
FIG. 3 is a view showing a situation in which the capsule type medical device is ingested into the living body, and electrical stimuli are applied in correspondence to various sites.

First, as shown in FIG. 3, after having put on the external device 3 via a belt or the like, the person who is the subject of investigation ingests the capsule type medical device 2 via mouth. It should be understood that, at this time, a switch upon the capsule type medical device 2 which is not shown is turned on, so that electrical power is supplied to the various structural components thereof from the battery 14. By doing this, the control section 6 operates the acquisition device 11, in other words the optical system 21 and the imaging element 20.

The capsule type medical device 2 which has been ingested to within the living body, along with taking images various portions within the living body with the imaging element 20 while shifting along the alimentary canal, also sends these images to the external device 3 by the wireless transmission and reception section 12. On the other hand, the external device 3, along with receiving these images via the wireless transmission and reception section 31, also performs image processing and the like upon these images with the control section 33, and performs recording of them in the recording device 32, as required.

Figure 4:
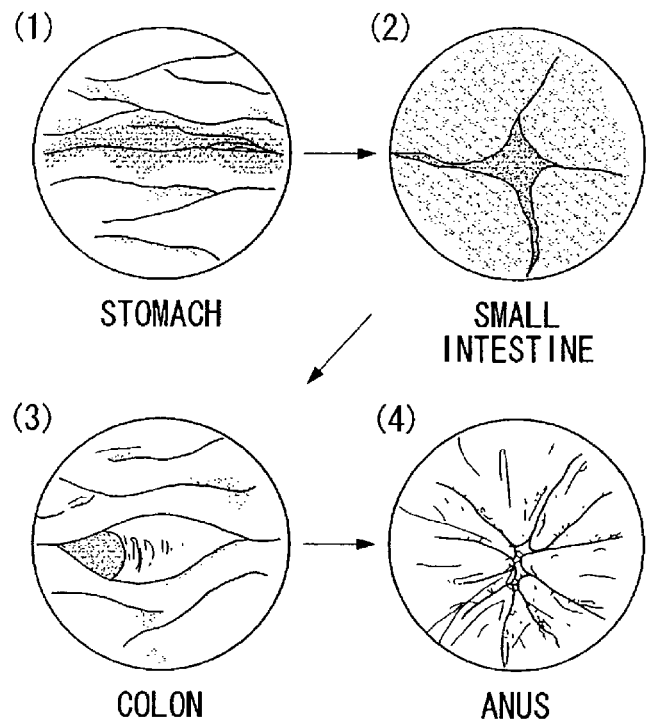
FIG. 4 is a figure showing an example of the positioning of images which have been taken images by the capsule type medical device of the stomach, the small intestine, the colon, and the anus.

Thus, as shown in FIG. 3, when the capsule type medical device 2 has arrived at the stomach of the patient, the imaging element 20 sends an image of the stomach to the external device 3, as shown in FIG. 4. By comparison of the brightness or the color or the frequency distribution of the image, or the surface properties of the mucosa or the like, for the image which has been sent and has arrived and for the set image, the position detection circuit 4 of the external device 3 detects that the capsule type medical device 2 is positioned at the stomach of the patient. In this case, the control section 33 does not perform transmission of any control signal.

Next, as shown in FIG. 3, when the capsule type medical device 2 has passed through the stomach and has arrived at the small intestine, the imaging element 20 sends images of the small intestine to the external device 3, as shown in FIG. 4. The position detection circuit of the external device 3 detects that the capsule type medical device 2 is positioned in the small intestine by comparing together the image which has been sent and the set image with regard to their brightness or color or frequency distribution of the image, or the surface properties and condition of the mucosa or the like. Upon receipt thereof, the control section 33 transmits a control signal for providing an electrical stimulus. At this time, the position detection circuit 4 detects the orientation of the capsule type medical device 2 from the image. In other words, it detects the shifting direction due to the peristaltic movement of the small intestine from the change of the image. For example, the position detection circuit 4 may detect whether the imaging element is oriented forwards or backwards, with respect to its direction of progress. That is, the position detection circuit 4 is able to decide whether the electrodes 5 at the one end or at the other end are positioned on the side of the direction of progress. Upon receipt of the result thereof, the control section 33 transmits a control signal so as to apply an electrical stimulus from one or the other of these electrodes 5.

It should be understood that, in this embodiment, it is supposed that the imaging element 20 is positioned to the side of the direction of progress, in other words, that the electrodes 5 on the one end of the capsule are positioned to the side of the direction of progress.

Figure 5:
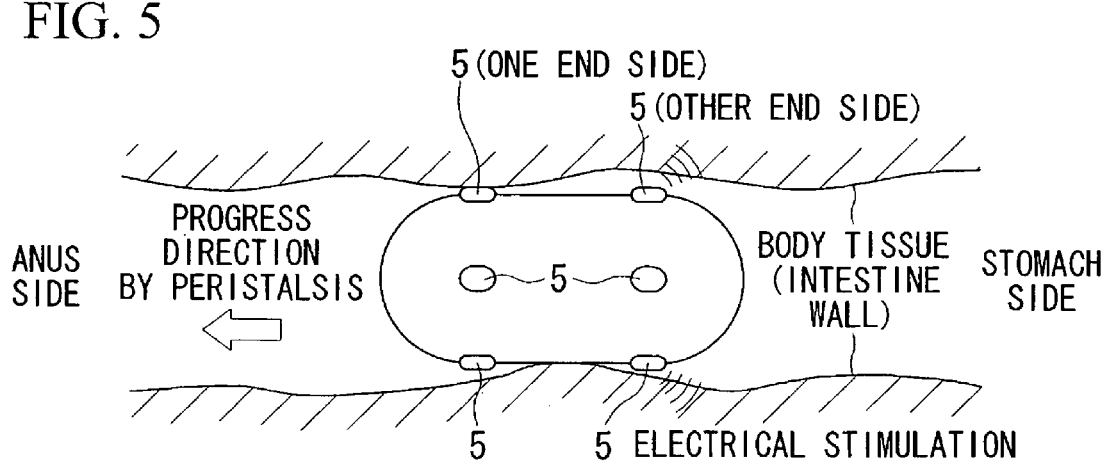
FIG. 5 is a figure showing a situation in which an electrical stimulus is being applied to living body tissue by the capsule type medical device within the small intestine.

When the capsule type medical device 2 has arrived at the small intestine, the wireless transmission and reception section 12 receives a control system which has been transmitted from the external device 3. Upon receipt of this control signal, the control section 6 supplies an electric current with the current generation circuit 23 to the electrodes 5 at the other end of the capsule, as shown in FIG. 5. These other end electrodes 5 to which this electric current has been supplied apply an electrical stimulus to the living body tissue of the small intestine (i.e. to the intestinal wall), and thereby shrink it. By shrinking this living body tissue, the capsule type medical device 2 proceeds along the direction of progress so as to shove aside the living body tissue. Accordingly, it is able to shift within the small intestine faster than the speed of shifting due to the peristaltic movement of the small intestine, and it is able to perform observation within the small intestine efficiently over a shortened time period.

Figure 2:
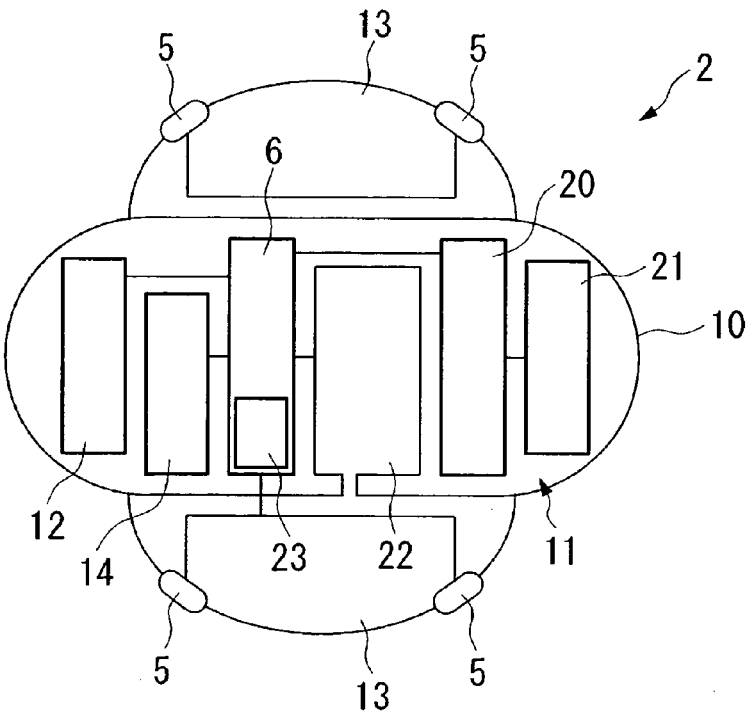
FIG. 2 is a sectional view showing a situation in which a balloon of the capsule type medical device has been expanded.

Furthermore when, as shown in FIG. 3, the capsule has passed along the small intestine and has arrived at the colon, the imaging element 20 transmits images of the colon to the external device 3, as shown in FIG. 4. In the same manner as described above, the position detection circuit 4 of the external device 3 detects the fact that the capsule type medical device 2 has arrived at the colon from these images, and the control section 33 sends a control signal corresponding to the colon to the capsule type medical device 2. In other words, along with applying an electrical stimulus from the electrodes 5 at the other end of the capsule, the control section 33 also transmits a control signal by wireless so as to cause the balloon 13 to expand. Upon receipt thereof, as shown in FIG. 2 and FIG. 3, in the capsule type medical device 2, the control section 6 operates the expansion and shrinkage mechanism 22 so as to cause the balloon 13 to expand. By doing this, it is possible to apply an electrical stimulus in the state in which the electrodes 5 are pressed closely and in a reliable manner against the living body tissue of the colon (the intestinal wall) which is comparatively large in size, as compared to the small intestine, so that, in the same way as for the small intestine, it is possible to shorten the time period required for performing the examination efficiently, and moreover while driving the capsule in a stabilized manner.

As shown in FIG. 3, when the capsule has passed through the colon and has arrived at the anus, the imaging element 20 transmits an image of the anus to the external device 3, as shown in FIG. 4. In the same manner as described above, the position detection circuit 4 of the external device 3 detects the fact that the capsule type medical device 2 has arrived at the anus from this image, and the control section 33 transmits a control signal corresponding to the anus to the capsule type medical device 2. In other words, the control section 33 wirelessly sends a control signal which, along with shrinking down the balloon 13, also causes the electrical stimulation from the electrodes 5 on the other end of the capsule to be stopped. Upon receipt of this signal, as shown in FIG. 3, in the capsule type medical device 2, the control section 6 causes the expansion and shrinkage mechanism 22 to operate, and thus, by shrinking down the balloon 13, returns it to its original state. By doing this, the excretability of the capsule type medical device 2 after the examination procedure has been completed is enhanced.

On the other hand, a doctor or the like performs diagnosis of the state of health of the person who is the subject of investigation, based upon images which are recorded in the recording device 32 of the external device 3, which are in-vivo information.

According to the capsule type medical device system 1 described above, since it is possible to apply an electrical stimulus to living body tissue which corresponds to a site within the living body, accordingly it is possible to perform observation with good efficiency. Furthermore, it is possible to ensure stabilized operation while suppressing useless consumption of the energy in the battery 14. Since the electrical stimulation is not performed at a site such as, for example, the stomach or the like at which the effectiveness of electrical stimulation is low, accordingly it is possible to ensure that wasteful operation does not occur. Furthermore, by providing the external device 3 which has a complicated structure such as the position detection circuit 4 and the like, it is possible to reduce the structure of the capsule type medical device 2 to the minimum limit possible, and accordingly it is possible to anticipate an enhancement in its compactness.

Yet further, since not only are images taken advantage of as in-vivo information, but also they are taken advantage of as positional detection information for the position detection circuit 4, accordingly no structure is required for detecting separate information for this position detection. Accordingly, it is possible to anticipate a simplification of the structure of the device.

Even further, since the balloon 13 is provided, even in the case of a site which affords a comparatively wide space such as the colon, it is possible to adhere the electrodes 5 securely against the living body tissue and to apply an electrical stimulus thereby. Still further, since, along with arranging the electrodes 5 at the one end and at the other end of the capsule, also the control section 6 performs control of the electrical stimulation device 14 in correspondence to the orientation of the capsule type medical device 2 which has been detected by the position detection circuit 4, accordingly it is possible to perform trustworthy control of the shift direction, irrespective of the attitude within the living body of the capsule endoscope 2.

It should be understood that although, in the above described first embodiment, the capsule type medical device 2 included the balloon 13, this is not limitative; it would be acceptable for no such balloon 13 to be incorporated. In such a case, it would be acceptable to affix the electrodes 5 so that they are positioned upon the outer surface of the casing 10.

Figure 6:
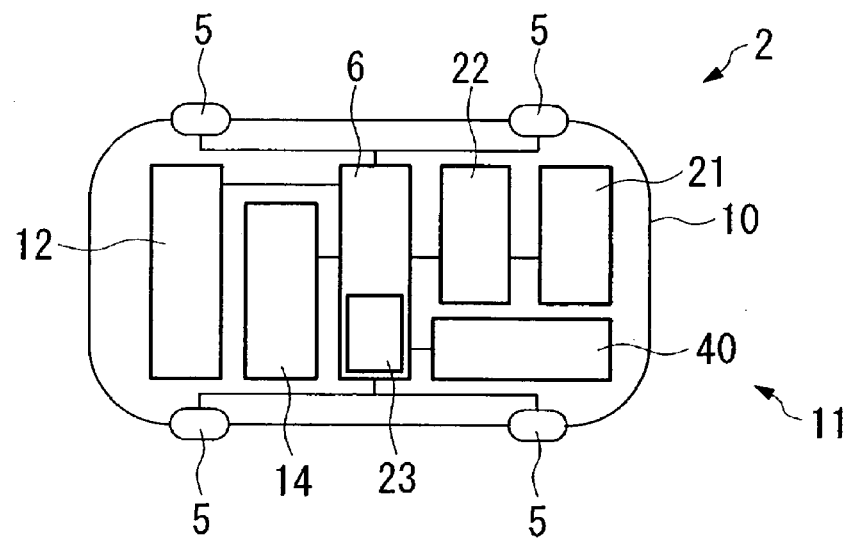
FIG. 6 is a sectional view showing a capsule type medical device which includes a pH sensor.

Furthermore, although, as a position detection device for detecting the position of the capsule type medical device 2 within the living body, the position detection circuit 4 is assembled to the control section 33 of the external device 3, and the position of the capsule type medical device 2 is detected based upon images, which are in-vivo information, which are captured by the imaging element 20, this is not to be considered as limitative. For example, it would also be acceptable, as shown in FIG. 6, for the acquisition device 11 of the capsule type medical device 2 to include a pH sensor 40 which measures the pH value within the living body, and for the position detection circuit 4 to detect the position of the capsule type medical device 2 based upon the pH value which is measured by this pH sensor 40. In this case, it would be acceptable to arrange for it to be possible to perform mutual communication of the pH value (information) between the wireless transmission and reception section 12 of the capsule type medical device 2 and the wireless transmission and reception section 31 of the external device 3. By doing this, the position detection circuit 4 is able, for example, to compare the pH value which has been measured with a threshold value which has been set in advance, or the like. Furthermore, the position detection circuit 4 is able to detect the position of the capsule type medical device 2 within the living body based upon changes of the pH value which is measured (such as, for example, whether this pH value is the acidity within the stomach, or whether it has changed to the neutrality in the small intestine), or the like. In particular, it is possible to anticipate a simplification of the algorithm used, as compared with the positional detection according to images of the first embodiment.

Figure 7:
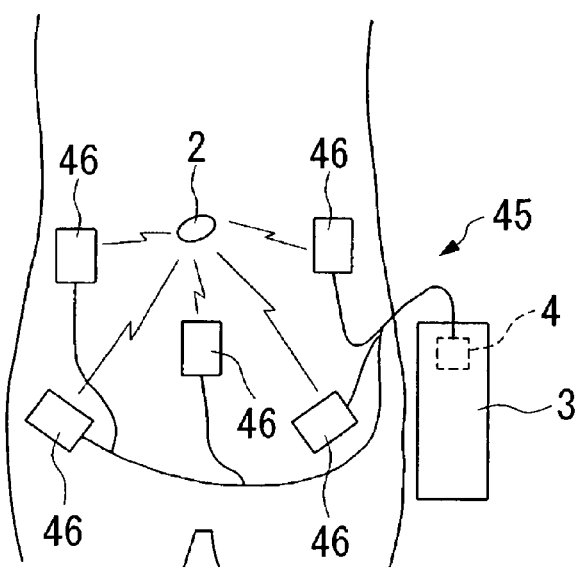
FIG. 7 is a figure showing an example of a position detection device which detects the position of the capsule type medical device, by taking advantage of radio wave strength.

Yet further, it would also be acceptable to make the position detection device so that it detected the position of the capsule type medical device 2, based upon the strength of the radio waves which are transmitted from the capsule type medical device 2. That is, as shown in FIG. 7, it would be acceptable to provide a structure in which the wireless transmission and reception section 12 of the capsule type medical device 2 is made to be capable of generating wireless radio waves, and in which the position detection device 45 included a plurality of reception antennas 46 which measured the radio wave strength of the wireless radio waves which are provided to the external device 3, so that the position of the capsule type medical device 2 is detected based upon the strength of the radio waves which are received by these reception antennas 46. It should be understood that, in this case, the above described position detection device 45 includes the reception antennas 46 and the position detection circuit 4. Furthermore, it would also be acceptable to arrange the specified locations of these reception antennas 46 so that they are positioned in the vicinity of, for example, the stomach, the small intestine, or the colon. By doing this, it is possible for the position detection circuit 4 to detect that the capsule type medical device 2 has arrived at the small intestine, when the radio wave strength which is received by the reception antenna 46 which is disposed in the vicinity of the small intestine reaches its highest value. It is possible to perform positional detection for the capsule type medical device 2 accurately by taking advantage of radio wave strength in this manner.

Figure 8:
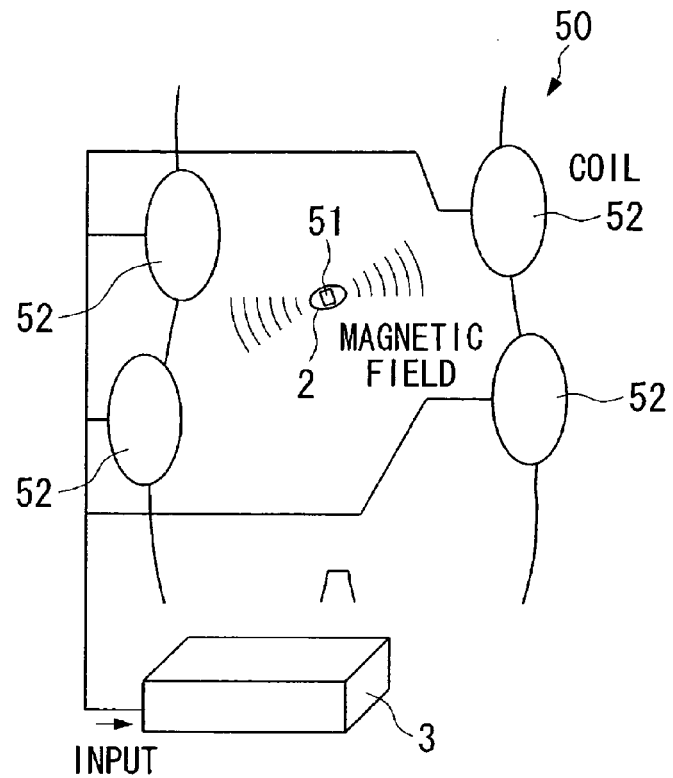
FIG. 8 is a figure showing an example of a position detection device which detects the position of the capsule type medical device, by taking advantage of magnetic field strength.

Furthermore, it would also be acceptable to make the position detection device so that it detects the position of the capsule type medical device 2 by taking advantage of magnetic field. In other words, as shown in FIG. 8, it would be acceptable to provide a structure in which the position detection device 50 includes a magnetic field generation device 51 not shown in the figure, such as a magnet or a coil or the like, provided to the capsule type medical device 2, which generates magnetic field, and a plurality of magnetic sensors, such as for example external coils (magnetic field detection device) 52, provided to the external device 3, which measure magnetic field, so that the position of the capsule type medical device 2 is detected based upon the magnetic field strength which has been measured by each of these external coils 52. In this case, it would be acceptable to arrange to dispose each of the external coils 52 so that it is positioned at a specific site such as, for example, the vicinity of the stomach, of the small intestine, or of the colon. By doing this, if the magnetic field strength which is measured by the external coil 52 which is disposed in the vicinity of the small intestine is the highest, then it is possible to detect that the capsule type medical device 2 has arrived at the small intestine. Furthermore, it would also be acceptable for the magnetic field generation device 51 in the position detection device 50 to be a coil which generated an alternating magnetic field. In this case it would become possible, by taking advantage of this alternating magnetic field, to implement position detection by using a magnetic sensor, in the state in which the interference environment due to physical quantities or the like which emanate from the environment is small. By taking advantage of magnetic field strength in this manner, it is possible to perform positional detection for the capsule type medical device 2 accurately. It should be understood that, apart from magnetic force, it would also be possible to perform the position detection in the same manner by using some other physical quantity, such as electromagnetic waves, radio waves, light, ultrasonic waves, or the like.

Figure 9:
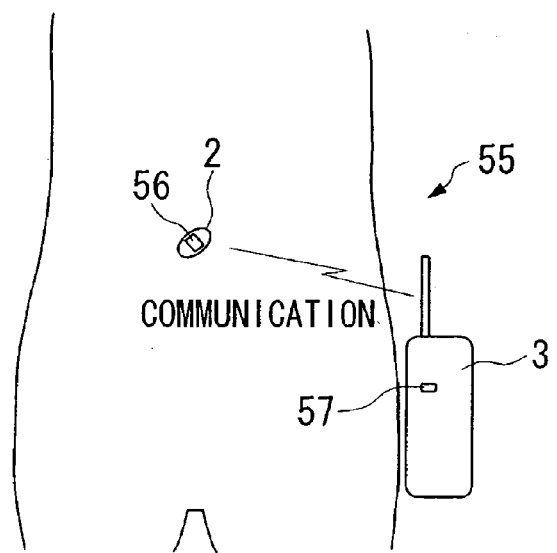
FIG. 9 is a figure showing an example of a position detection device which detects the position of the capsule type medical device, by taking advantage of acceleration information.

Furthermore, it would also be acceptable to make the position detection device so that it detected the position of the capsule type medical device 2 by taking advantage of acceleration information. In other words, as shown in FIG. 9, it would be acceptable for the position detection device 55 to include an acceleration sensor 56 internal to the living body, provided to the capsule type medical device 2, which, along with measuring the acceleration within the living body, transmits this acceleration information internal to the living body via the wireless transmission and reception section 12, and an acceleration sensor 57 external to the living body, provided to the external device 3, which measures acceleration external to the living body; and to be made so as to detect the position of the capsule type medical device 2 based upon the acceleration information internal to the living body which is received via the wireless transmission and reception section 31 of the external device 3, and the acceleration information external to the living body which is measured by the acceleration sensor 57 external to the living body.

In this case, for example, the acceleration sensor 57 external to the living body may perform position detection of the capsule type medical device 2 by, along with calculating the difference between these two items of acceleration information, also calculating the distance from this acceleration difference. By doing this, it is possible to perform position detection for the capsule type medical device 2 accurately by taking advantage of acceleration information. It should be understood that it would also be possible for the above described position detection device 55 as well, just like the above described position detection device 50, to perform position detection by using some other physical quantity, like electromagnetic waves, radio waves, light, ultrasonic waves or the like.

Figure 10:
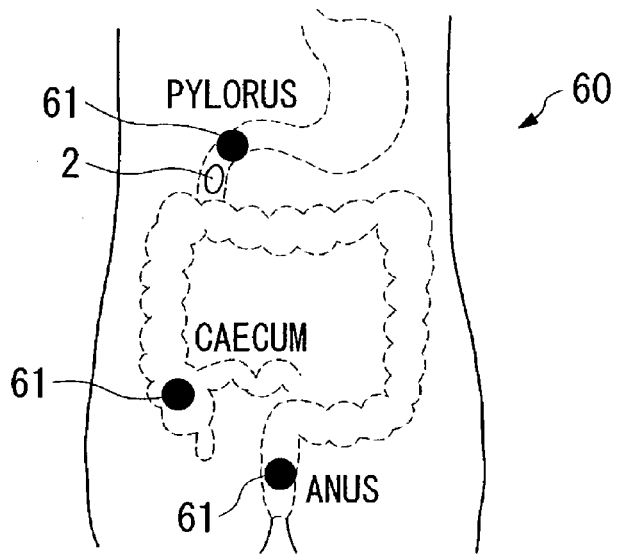
FIG. 10 is a figure showing an example of a position detection device which detects the position of the capsule type medical device, by taking advantage of magnetic field.

Furthermore, although the external device 3 is made to detect the position of the capsule type medical device 2, it would also be possible for the capsule type medical device 2 itself to constitute the position detection device, so as to detect its own position. As for example shown in FIG. 10, it would be acceptable for the position detection device 60 to include a plurality of magnets 61 which are disposed in the vicinity of specified sites outside the living body, and a magnetic sensor not shown in the figures, which is provided to the capsule type medical device 2, and which detects the magnetic field of the magnets 61; and to be made so as to detect the position of the capsule type medical device 2, based upon the magnetic field which has been detected by the magnetic sensor. It should be understood that, in FIG. 10, as the various specified sites, the magnets 61 are arranged in the vicinities of the pylorus portion of the stomach, of the caecum, and of the anus. By doing this, when the capsule type medical device 2 has arrived at the vicinities of the pylorus portion of the stomach, of the caecum, and of the anus, it is possible for the magnetic sensor to detect the magnetic field of the magnets 61 and thereby to detect its own position.

Figure 11:
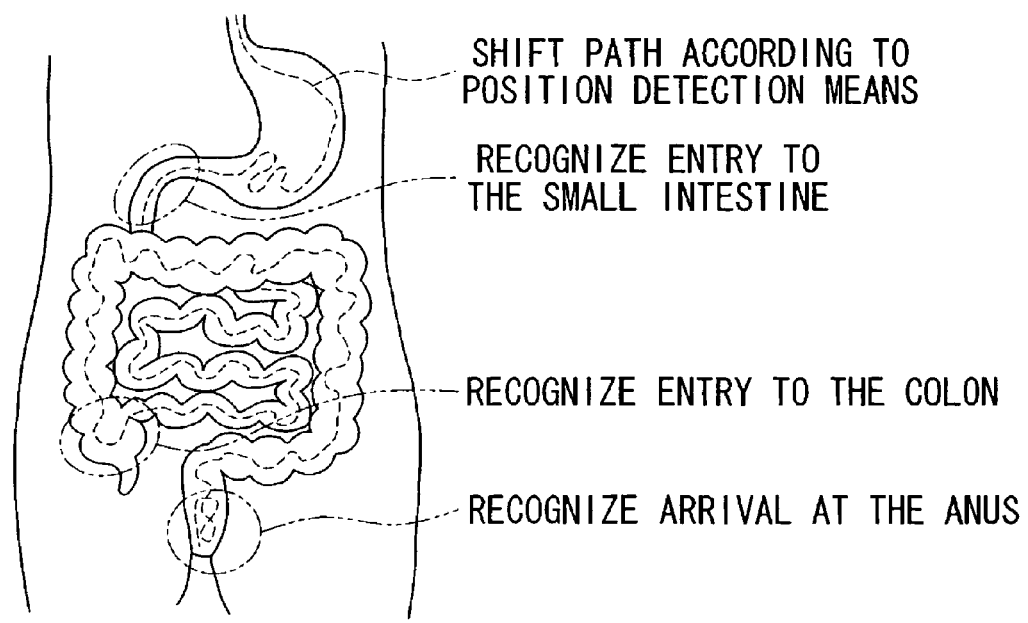
FIG. 11 is a figure showing an example of a position detection device which detects the position of the capsule type medical device, by taking advantage of the shift pattern of the capsule type medical device.

Yet further, it would also be acceptable, as shown in FIG. 11, along with setting up the position detection device so that, by taking advantage of the various position detection device described above, it recognizes the pattern of the shifting path of the capsule type medical device, also to set it up so that the control section 33 of the external device 3 specifies each of the sites, for example, the stomach, the small intestine, the colon, or the anus. By doing this, it is possible to detect the position of the capsule type medical device 2 from the pattern of the shifting path of the capsule type medical device 2. In particular, it is possible to anticipate a simplification of the algorithm, as compared with the case of detecting the position of the capsule type medical device 2 based upon images.

Figure 12:
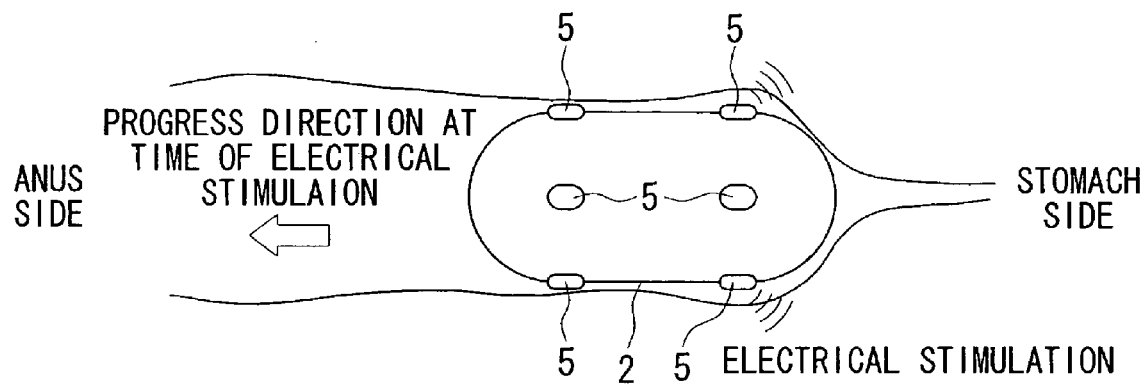
FIG. 12 is a figure showing a situation in which an electrical stimulus has been applied for a brief period to living body tissue, in order to detect the orientation of the capsule type medical device.

Even further, although, with the above described first embodiment, the position detection circuit is made so as to detect the orientation of the capsule type medical device, along with detecting its direction of shifting by the peristaltic movement within the small intestine from the changes of images, this is not to be considered as being limitative; for example, as shown in FIG. 12, it would also be acceptable to arrange to detect the orientation of the capsule type medical device 2 by taking advantage of the electrical stimulation. When, for example, the capsule type medical device 2 has arrived at the small intestine, an electrical stimulus is applied for a brief period to the living body tissue by the electrodes 5 at the one end or at the other end of the capsule, so that the capsule is caused to shift. By detecting the direction of shifting of the capsule type medical device 2 at this time, the detection of the capsule type medical device 2 is performed over a slower time period. After this, electrical stimulation may be applied to living body tissue from the electrodes 5 at the one end of the capsule or from its other end, according to its orientation.

Figure 13:
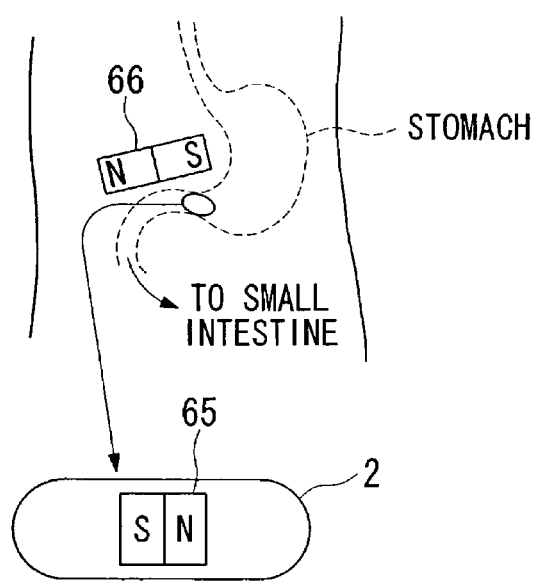
FIG. 13 is a figure showing an example in which permanent magnets have been disposed outside the living body and within the capsule type medical device, in order to regulate the orientation of the capsule type medical device.

Still further, although it is arranged to detect the orientation of the capsule type medical device within the living body by the above described methods, it would also be acceptable to arrange to regulate the orientation of the capsule type medical device when it is passing a specific site. For example, as shown in FIG. 13, along with providing a permanent magnet 65 in the interior of the capsule type medical device 2, a permanent magnet 66 might be provided in the vicinity of a specific site for example, in the vicinity of the small intestine. By doing this, when the capsule type medical device 2 passes the stomach and shifts within the small intestine, the capsule type medical device 2 shifts within the small intestine in a state in which its orientation is regulated to a fixed direction, due to its permanent magnet 65 and the permanent magnet 66 which is arranged in the vicinity of the small intestine. Furthermore, it would also be acceptable to utilize a coil, instead of the permanent magnet 65 which is provided to the capsule type medical device 2, or instead of the permanent magnet 66 which is provided to the specific site. By doing this, it is possible not to generate magnetic force at times other than when such force is required, and, for example, it is possible to keep down to the minimum possible limit the interference with and the influence upon the position detection device which takes advantage of magnetism as described above. Accordingly, it is possible reliably to cause progress in a constant direction, and it is easy to perform control of the electrical stimulation device.

Figure 14:
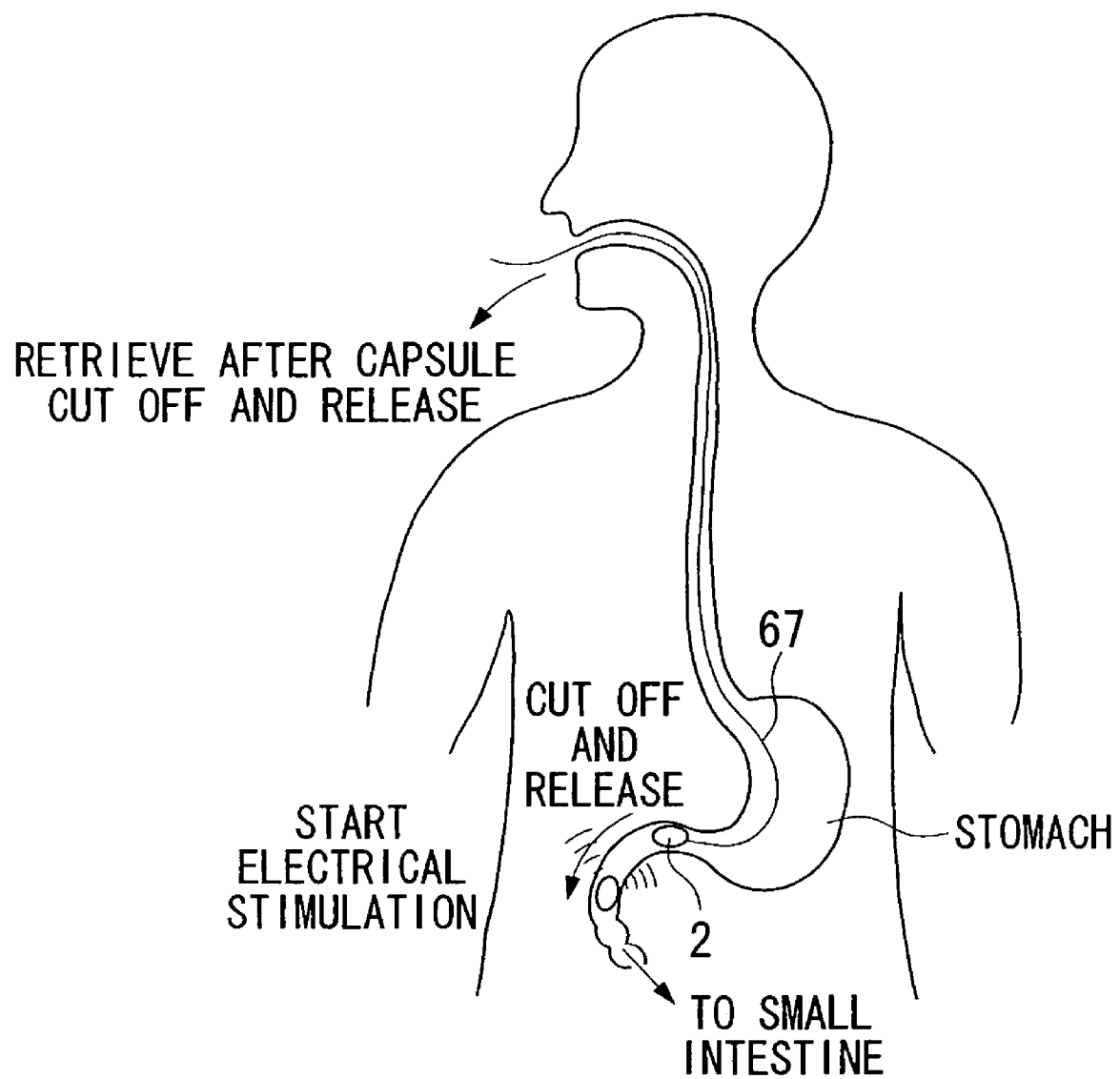
FIG. 14 is a figure showing a situation in which the capsule type medical device is ingested to within the living body, in a state in which a string is detachably attached to it, in order to regulate the orientation of the capsule type medical device.

It would also be acceptable to always use in parallel the orientation control function (the magnetic induction device) with magnetism described above, and to employ it in orientation control during observation. By doing this, the observational efficiency is enhanced. Moreover, not only is there the method with a magnet as described above, but it would also be acceptable, as for example shown in FIG. 14, to arrange to ingest the capsule type medical device 2 into the interior of the patient in a state in which a string 67 has been affixed to it which can be cut away from it, and to cut away the string 67, after it has been checked that the capsule has arrived at a specific site within the small intestine or the like. Since, by doing this, it is possible to cause the capsule type medical device 2 to progress in a fixed direction while reliably regulating its orientation, accordingly it is easy to perform control of the electrical stimulation device.

Although, in the above described first embodiment, it is arranged to transmit and to receive the in-vivo information with the wireless transmission and reception section 12 which is provided to the capsule type medical device 2, and with the wireless transmission and reception section 31 which is provided to the external device 3, it would also be acceptable, instead of the above, to emanate the in-vivo information from a transmission section which is provided to at least one of the capsule type medical device 2 and the external device 3, and to detect this in-vivo information with a detection section which is provided to the other one thereof.

In the above described first embodiment, it would also be acceptable for the device which applies an electrical stimulus, such as the electrodes 5 or the like which are provided to the capsule type medical device 2, to have a structure like the following.

Figure 15:
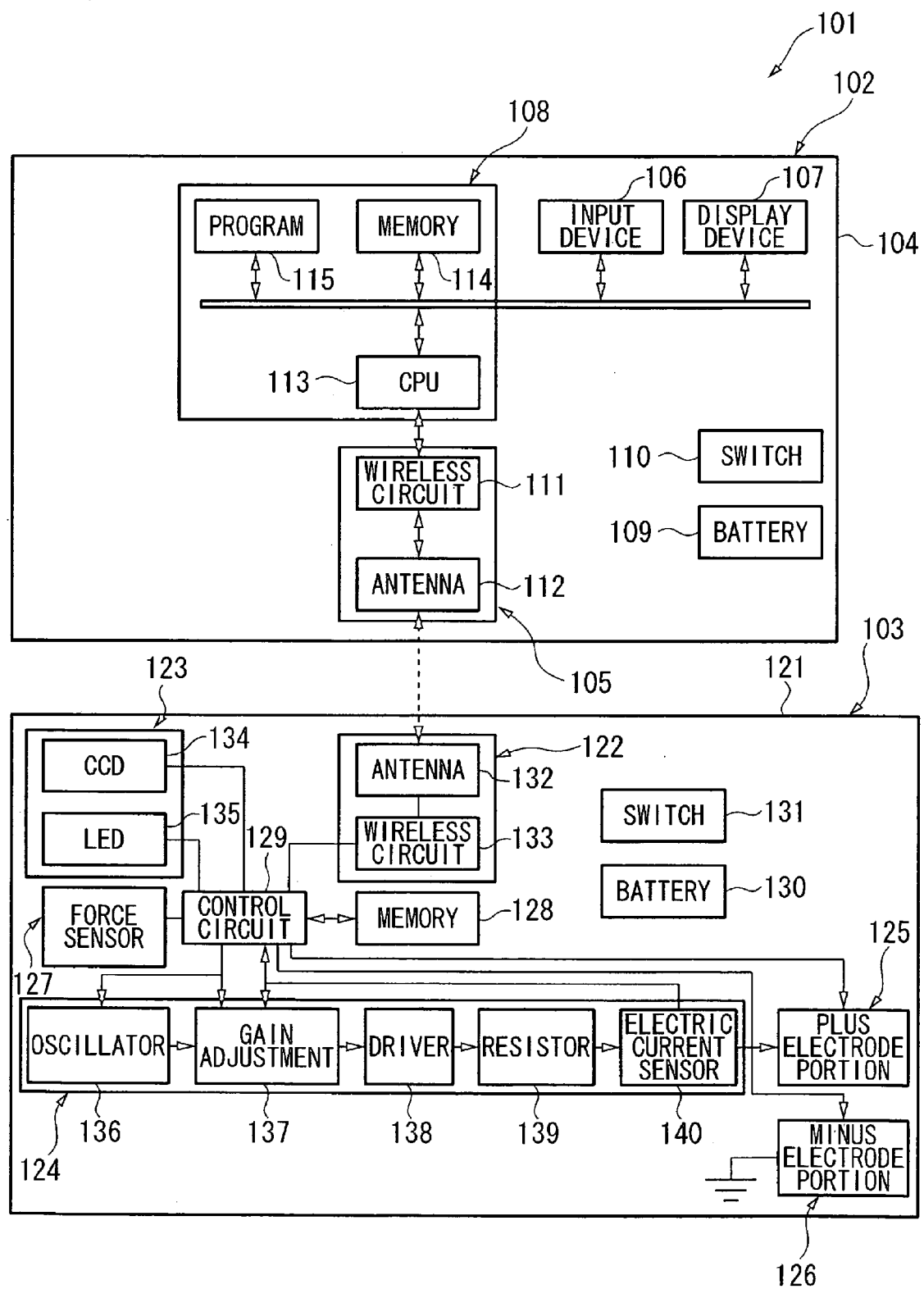
FIG. 15 is a simplified structural diagram showing a first variant example of the first embodiment of the capsule type medical device system according to the present invention.

A first variant example of the first embodiment of the capsule type medical device system of the present invention will now be described in detail with reference to the figures. As shown in FIG. 15, this capsule type medical device system 101 includes an external device 102 which is disposed outside the living body, and a capsule type medical device 103 which can be ingested to within the living body (to within his living body).

The device 102 external to the living body includes, within a main body case 104, a wireless transmission and reception section (an external communication device) 105 which transmits and receives information to and from the capsule type medical device 103, an input device 106, a display device 107, an external control section 108 which controls these various structural elements (device), a battery 109 which supplies electrical power to these various structural elements, and another actuation switch 110.

The wireless transmission and reception section 105 includes a wireless circuit 111 and an antenna 112, and is equipped with the functions of receiving images, which are in-vivo information, which have been transmitted and have arrived from the capsule type medical device 103, and of sending them to the external control section 108. The input device 106 is a keyboard, a mouse, a joystick, a touch panel, a switch, or the like which receives data input and actuation. The display device 107 displays information about the current capsule type medical device 103, and displays the in-vivo information which has been received from that capsule type medical device 103. Furthermore, it also displays a GUI (Graphical User Interface) which supports input actuation.

The external control section 108 is structured to include a CPU (a central processing unit) 113, a memory 114 (a storage device) which stores in-vivo information and data, a memory 115 for program storage which stores a program which performs control of the external device, and a communication interface (a bus).

The capsule type medical device 103 which is ingested into the test subject includes a capsule 121, which is a casing tightly enclosing the interior, and which is made from a plastic or the like; and, in the interior of this capsule, it includes a wireless transmission and reception section 122 (an internal communication device) which transmits and receives information to and from the device 102 external to the living body, an acquisition device 123 which acquires in-vivo information, a current generation device 124 which generates an electric current which has a specific waveform, a plus electrode portion 125 and a minus electrode portion 126 which contact against living body tissue, a sense of force sensor (a contact detection device) 127 which measures the contact pressure with which this plus electrode portion 125 and this minus electrode portion 126 contact against living body tissue, a memory 128 (a storage device) which stores for a brief period the image data which has been acquired by the acquisition device 123, a control circuit (control section) 129 which controls these various structural elements, a battery 130 which supplies electrical power to these various structural elements, and a switch 131 which turns the power supply ON or OFF.

It should be understood that the current generation device 124 and the plus electrode portion 125 and the minus electrode portion 126 constitute an electrical stimulation device which applies electrical stimuli to living body tissue.

The wireless transmission and reception section 122 includes an antenna 132 and a wireless circuit 133, and it transmits in-vivo information to the device 102 external to the living body, and receives signals which the device 102 external to the living body outputs.

The acquisition device 123 includes a CCD (Charge Coupled Device) 124 and a LED (Light Emitting Diode) 135 which are provided within a transparent cover (not shown in the drawings) which is provided at one end of the capsule 121.

The CCD 134 is used for taking images various portions inside the living body, and thus acquiring images. The LED 135 illuminates the visual range of the CCD 134. It should be understood that, instead of the CCD 134, it would also be possible to provide a sensor which monitored the living body, such as a pH sensor or the like. Furthermore, instead of the acquisition device 123, it would also be possible to include a body sampling section which performed sampling of living body tissue, or a body treatment section which performed treatment of living body tissue. Yet further, it would also be possible to mount at least two of the acquisition device 123, the body sampling section, and the body treatment section, at the same time.

The current generation device 124 consists of an oscillator (a waveform generator) 136, a gain adjustment circuit 137, a driver 138, a resistor 139, and an electric current sensor 140.

The oscillator 136 generates an alternating current signal of a frequency of from a few Hz to a few tens of Hz. Furthermore, according to information from the control circuit 129, it is able to generate any desired waveform pattern, such as DC output, square wave, sine wave, sawtooth wave, and the like. Yet further, in the case of a square wave, it is able to vary the ratio (the duty ratio) of the time periods when the amplitude is High state and when it is in Low state. For a sawtooth wave, it is able to adjust the ratio of the time period while the voltage is rising to the time period when it is dropping. It should be understood that the selection of the waveform pattern for the oscillator 136, and of whether it is outputting or not outputting, is controlled by the control circuit 129.

The gain adjustment circuit 137 amplifies the output of the oscillator 136. The amplification ratio is controlled by the control circuit 129. Furthermore, the gain adjustment circuit 137 also functions as a limitation circuit which monitors the output of the electric current sensor 140, and, if this electric current which flows is greater than a set value, lowers the gain and limits the electric current value.

The driver 138 is connected to the output of the gain adjustment circuit 137, and is a circuit which performs voltage electric current transfer in order to control the electrical stimulus which is applied to living body tissue with an electric current value.

The resistor 139 controls the electric current which flows to the living body, and is for preventing excess electric current; one of its ends is connected to the output of the driver 138, while its other end is connected to the plus electrode portion via the electric current sensor 140.

The electric current sensor 140 measures the electric current value which is supplied from the resistor 139 to the plus electrode portion 125, in other words the electric current value which is applied to the living body. The output of this electric current sensor 140 is connected to the control circuit 129 and the gain adjustment circuit 137.

Figure 16:
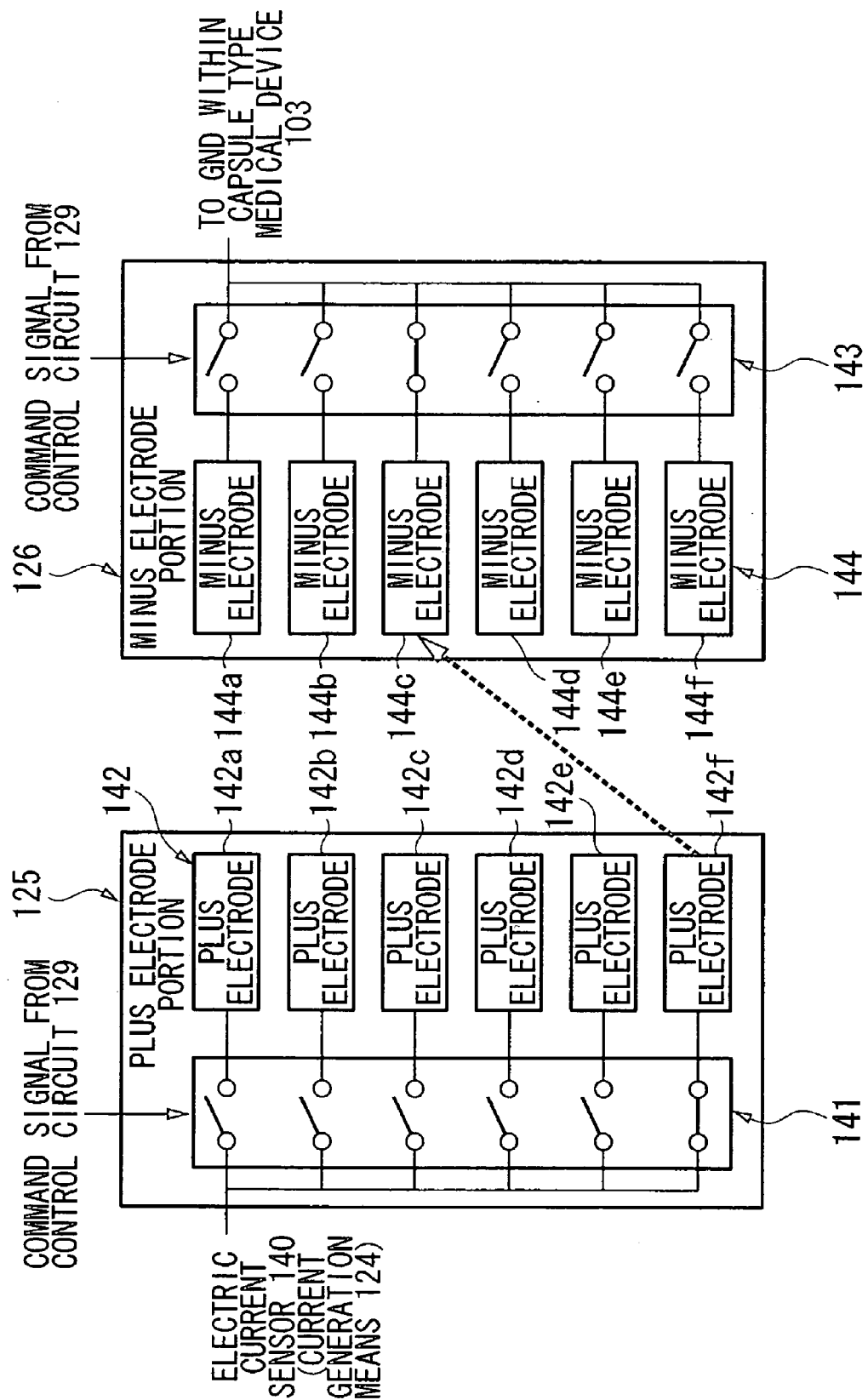
FIG. 16 is a view showing the structure of a plus electrode portion and a minus electrode portion.

As shown in FIG. 16, the plus electrode portion 125 includes a switching element 141 (a first switching device) which is connected to the electric current sensor 140, and plus electrodes 142 which is connected to this switching element 141. These plus electrodes 142 are one set of electrodes which are connected to the high electrical potential side, and, in this first variant example, there are six of these plus electrodes 142a through 142f. As will be described hereinafter, a portion of each of these plus electrodes 142a through 142f is exposed to the exterior of the capsule 121. The switching element 141 has six contact points, and each one of these is connected to one of the plus electrodes 142a through 142f. These contact points of this type of switching element 141 are changed over, based upon command signals from the control circuit 129.

The minus electrode portion 126 includes a switching element 143 (a second switching device) which is connected so as to be at the same electrical potential as the ground of the other circuits within the capsule type medical device 103 (a standard electrical potential), and minus electrodes 144 which are connected to this switching element 143. These minus electrodes 144 are another set of electrodes which are connected to the low electrical potential side, and, in this first variant example, there are six of these minus electrodes 144a through 144f, corresponding to the number of the plus electrodes 142. A portion of each of these minus electrodes 144a through 144f, as will be described hereinafter, is exposed to the exterior of the capsule 121. The switching element 143 has six contact points, and each one of these is connected to one of the minus electrodes 144a through 144f. These contact points of this type of switching element 143 are changed over, based upon command signals from the control circuit 129.

Figure 17:
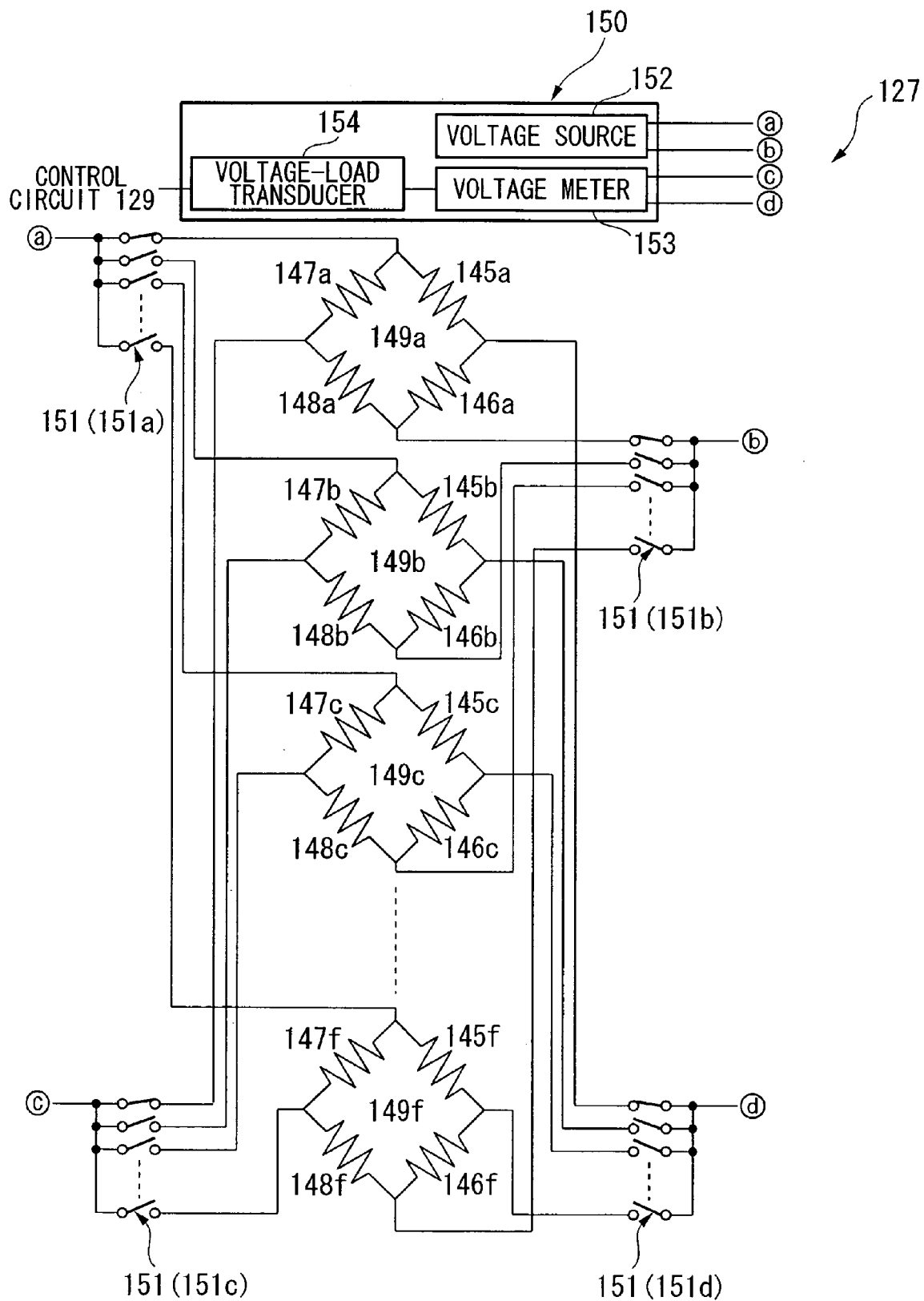
FIG. 17 is a view showing the structure of a sense of force sensor.

As shown in FIG. 17, the sense of force sensor 127 includes: deformation gauges 145a through 145f, 146a through 146f, 147a through 147f, and 148a through 148f which are each respectively fitted to the plus electrodes 142a through 142f (refer to FIG. 16) and the minus electrodes 144a through 144f (refer to FIG. 16); an amp 150 for deformation gauging which detects the voltages of bridge circuits 149a through 149f which are constituted by the deformation gauges 145a through 148f; and a switching circuit 151 for deformation gauging which changes over the one of the bridge circuits 149a through 149f whose voltage is detected by the amp 150 for deformation gauging.

The amp 50 for deformation gauging is a device which monitors the contact pressure of the electrodes 142a through 142f and 144a through 144f against living body tissue, and it includes a voltage source 152 which applies a predetermined voltage to the bridge circuits 149a through 149f, a voltage meter 153 which measures the voltage of the bridge circuits 149a through 149f, and a voltage load transducer 154 which is connected to the voltage meter 153. This voltage load transducer 154 converts the voltage which has been detected by the voltage meter 153 into an amount of force (a pressure). The output of this voltage load transducer 154 is connected to the control circuit 129.

The switching circuit 151 for deformation gauging includes a switching circuit 151a which is connected to the high electrical potential side of the voltage source 152 of the amp 150 for deformation gauging, a switching circuit 151b which is connected to the low electrical potential side of the voltage source 152, a switching circuit 151c and a switching circuit 151d which are connected to the input of the voltage meter 153. Each of the switching circuits 151a through 151d has six contact points corresponding to the numbers of the electrodes 142a through 142f and 144a through 144f. In the switching circuit 151a and the switching circuit 151b, the contact points are connected by the control circuit 129 so that voltage is applied to one of the bridge circuits 149a through 149f. Furthermore, in the switching circuit 151c and the switching circuit 151d, the contact points are connected by the control circuit 129 so that the voltage which is generated by the bridge circuit 149a through 149f to which voltage is applied can be measured.

The bridge circuits 149a through 149f include four deformation gauges. For example, the bridge circuit 149a includes the four deformation gauges 145a, 146a, 147a, and 148a. The one end of the deformation gauge 145a and the one end of the deformation gauge 147a are connected to the same contact point of the switching circuit 151a, and the one end of the deformation gauge 146a and the one end of the deformation gauge 148a are connected to the same contact point of the switching circuit 151b. Furthermore, the other end of the deformation gauge 147a and the other end of the deformation gauge 148a are connected to the same contact point of the switching circuit 151c, and the other end of the deformation gauge 145a and the other end of the deformation gauge 146a are connected to the same contact point of the switching circuit 151d. It should be understood that, as will be described hereinafter, the deformation gauge 145a and the deformation gauge 146a are fitted to the plus electrode 142a. The deformation gauge 147a and the deformation gauge 148a are fitted to the minus electrode 144a which is disposed adjacent to that plus electrode 142a. Moreover, following this pattern, each of the bridge circuits 149b through 149 has the same structure as the bridge circuit 149a.

Figure 18:
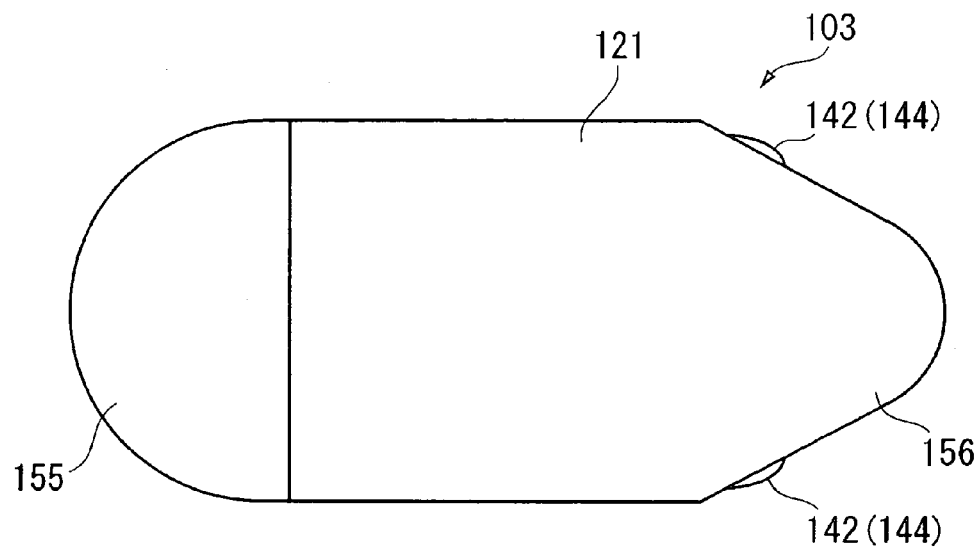
FIG. 18 is an external view of a capsule type medical device.
Figure 19:
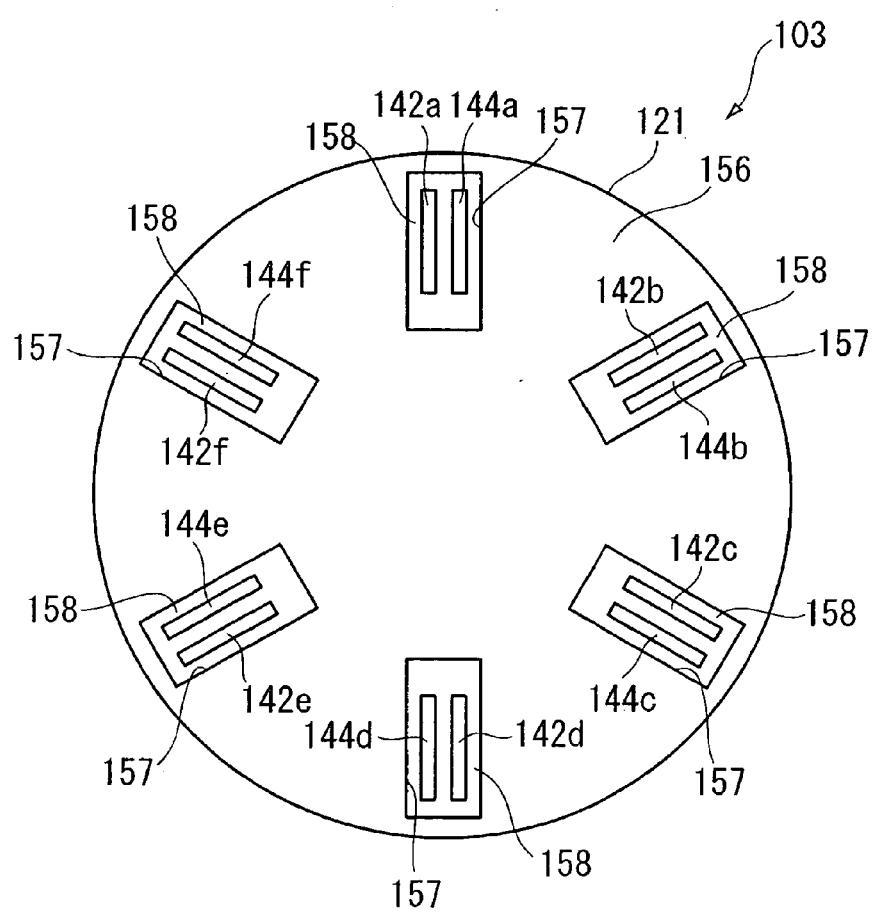
FIG. 19 is a view showing the external appearance of a rear portion of the capsule type medical device.

The shape of the capsule 121 of this capsule type medical deice 103, and an example of the arrangement of the plus electrodes 142 and the minus electrodes 144, will now be explained using FIG. 18, FIG. 19, and FIG. 20. It should be understood that FIG. 18 is an external view of the capsule type medical device. FIG. 19 is a figure showing the external appearance of its rear portion, while FIG. 20 is a sectional view in the vicinity of the rear portion.

As shown in FIG. 18, the capsule 121 is shaped as a circular cylinder, and one tip portion 155 thereof, which is its one end which is positioned at the left side in the figure, has a curved surface which is close to a hemisphere. A transparent portion is provided upon this tip portion 155, and the acquisition device 123 and so on are disposed at the interior thereof. Furthermore, the outer diameter of the rear portion 156, which is the other end which is positioned at the right side in the figure, is reduced linearly more than is the tip portion 155, and its final rear end is closed by a rounded shape. It should be understood that although, in the following, the explanation is made in terms of the tip portion 155 being the front end of this capsule type medical device 103 with respect to its direction of progress, it may also happen that the front and the rear of the capsule type medical device 103 are reversed within the coelom.

As shown in FIG. 19, six openings 157 are formed radiating outwards upon this rear portion 156 at equal intervals. These openings 157 have roughly rectangular forms, facing from the central axis towards the side surface of the capsule 121 (its peripheral edge in FIG. 19), and, in each of them, the plus electrodes 142a through 142f and the minus electrodes 144a through 144f are respectively arranged so as to be in parallel, and moreover so that the one portions of each of their ends are projected to the outside. In concrete terms, in each of the openings 157, the electrode 142a and the electrode 144a, the electrode 142b and the electrode 144b, the electrode 142c and the electrode 144c, the electrode 142d and the electrode 144d, the electrode 142e and the electrode 144e, and the electrode 142f and the electrode 144f, are respectively arranged so as to be in parallel. It should be understood that the gaps which are formed in the openings 157 in the state in which the electrodes 142 and 144 are inserted into them are filled up with a soft adhesive material 158, so that they become watertight constructions. By using this soft adhesive material 158, it becomes possible to measure the contact pressure between the electrodes 142 and 144 and the living body tissue with the deformation gauges 145a through 148f.

Figure 20:
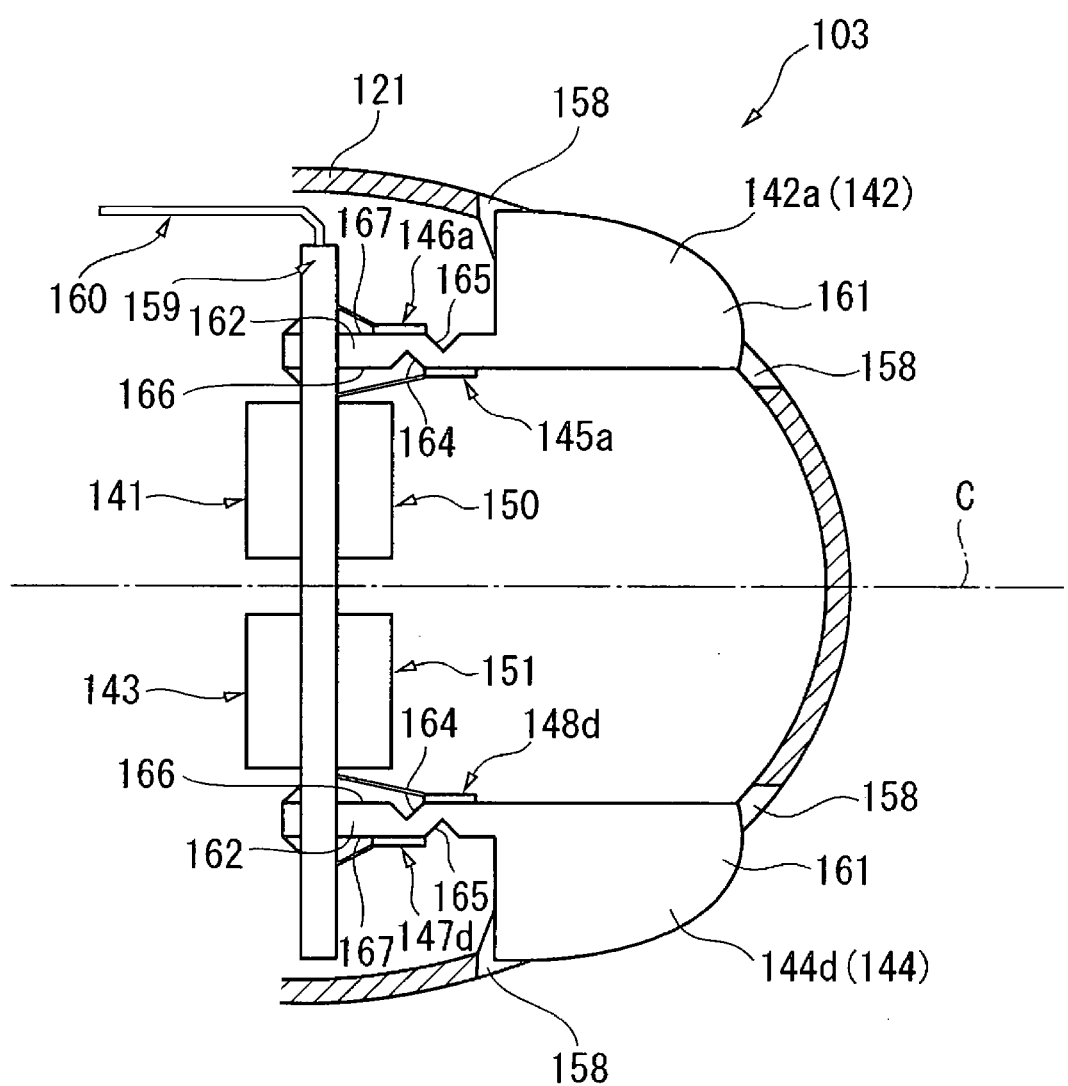
FIG. 20 is a sectional view of the rear portion of the capsule type medical device.

As shown in FIG. 20, in the interior of the capsule 121, there is fixed an electrical circuit substrate 159. Upon this electrical circuit substrate 159, there are fitted the plus electrodes 142 (only the plus electrode 142a is shown in FIG. 20) and the minus electrodes 144 (only the minus 144d is shown in FIG. 20), the switching elements 141 and 143, and the amp for deformation gauging 150 and the switching circuit 151 for deformation gauging of the sense of force sensor 127.

Furthermore, a flexible substrate 160 is fitted at one end of the electrical substrate 159. This flexible substrate 160 is used for exchanging signals from the various circuits upon the electrical substrate 159 with the control circuit 129. Furthermore, it also serves the purposes of supplying source power to the various circuits upon the electrical circuit substrate 159, and of electrically connecting together the electric current sensor 140 and the plus electrode portions 125.

The plus electrodes 142 include contact portions 161, the one ends of which project from the capsule 121, and base portions 162 which extend from these contact portions 161; and these base portions 162 are mounted to the electrical circuit substrate 159.

Portions of elongated portions of these contact portions 161 are formed in the shape of curved surfaces whose shape is approximately the same as that of the slope of the capsule 121, and portions of these curved surfaces are exposed at the exterior of the capsule 121. In concrete terms, they include a bottom surface which follows along the central axis C, and a plane surface which extends outwards in the radial direction of the capsule 121 from the tip portion 155 side of the bottom surface (refer to FIG. 18); and a curved surface is formed from the position of the tip end of the plane surface (its outer end in the radial direction), towards the position of the tip end of the bottom surface (its rear end along the central axis C).

The base portion 162 has a shape which extends along the central axis C from the plane surface of the contact portion 161, and which is longer and thinner than the contact portion 161. Furthermore, V grooves 164 and 165 are formed between the contact portions 161 and the portions which are fitted to the electrical circuit substrate 159. The V groove 164 is provided upon the surface 166 which extends along the lengthwise direction of the capsule 121 and faces the central axis C, so as to be orthogonal to the lengthwise direction along the central axis C. Moreover, the V groove 165 is provided upon the surface 167 which is on the other side from the surface 166, and is provided more towards the contact portions 161 than the V grooves 164, again so as to be orthogonal to the lengthwise direction along the central axis C. The V groove 164 makes the base portion 162 easily bent towards the central axis C direction, while the V groove 165 makes the base portion 162 easily bent towards the direction which is opposite to the central axis C direction. Therefore, if a force in the direction of the central axis C acts upon the contact portion 161 of the electrode 142, or if a force of the opposite orientation acts thereupon, the base portion 162 bends in the vicinities of the V grooves 164 and 165, and is deformed so as to yield to this type of force. With this type of plus electrode 142, the deformation gauge 145$a$ of the sense of force sensor 127 is fitted at a site on the surface 166 more towards the contact portion 161 than the V groove 164. Furthermore, the deformation gauge 146$a$ of the sense of force sensor 127 is fitted at a site on the surface 167 more towards the electrical circuit substrate 159 than the V groove 165.

Furthermore, the minus electrodes 144 as well have the same structure. That is, a V groove 164 is provided upon the surface 166 side of the base portion 162, and a V groove 165 is formed on its surface 167 side; and, if a force in the direction of the central axis C, or a force in the other direction, acts upon the contact portion 161, the base portion 162 in the neighborhood of the V grooves 164 and 165 bends. The deformation gauge 148$d$ of the sense of force sensor 127 is fitted at a site on the surface 166 more towards the contact portion 161 than the V groove 164. Furthermore, the deformation gauge 147$d$ of the sense of force sensor 127 is fitted at a site on the surface 167 more towards the electrical circuit substrate 159 than the V groove 165.

It should be understood that the reason for the four deformation gauges which constitute each one of the bridge circuits 149$a$ through 149$f$ being fitted so as to be distributed between one adjacent set of a plus electrode 142 and a minus electrode 144, is because the set of a plus electrode 142 and a minus electrode 144 which are adjacent in this manner exhibit behavior almost like one body, and are in the same contact state in relation to living body tissue.

Observation within the body of the test subject with a capsule type medical device system 101 which has this type of structure will now be explained in the following.

First, the test subject is insulated, and the device 102 external to the living body is fitted to his body portion with a belt or the like. Next, the capsule type medical device 103 is ingested into the test subject via mouth. This capsule type medical device 103, upon command from the device 102 external to the living body, or upon command from a timer circuit or an operational program which is provided to the control circuit 129, along with emitting light from the LED 135, also operates the CCD 134, and takes images of the inside of the living body. The image data which has been acquired by this image is digitalized, and is stored for a brief period in the memory 128 in a compressed state, according to requirements. This image data which has been stored in the memory 128 is transmitted via the wireless transmission and reception section 122 to the device 102 external to the living body.

In the device 102 external to the living body, the image data which has been received by the wireless transmission and reception section 105 is data processed by the CPU 113 within the control section 108 external to the living body, and is stored in the memory 114. The images of the inside of the living body which have been taken images by the capsule type medical device 103 are thus accumulated in the memory 114 of the device 102 external to the living body. Furthermore, according to requirements, these images are outputted upon a display device 107.

The external control section 108 compares together two images which have been taken images by the capsule type medical device 103 at different time instants, and infers the shift amount of the capsule type medical device 103 within the coelom. As a method for inferring the shift amount, for example, a correlation method of image processing may be utilized. In the external control section 108, a threshold value for the correlation coefficient is set in advance, and, if the correlation coefficient of two images which follow one another in time is greater than the threshold value, then it is decided that the shift amount of the capsule type medical device 103 is insufficient. On the other hand, if the correlation coefficient is less than the threshold value, then it is decided that the capsule type medical device 103 is shifting within the coelom.

If it is decided that the shift amount of the capsule type medical device 103 is small, and moreover when shifting of the capsule type medical device 103 is required, then the capsule type medical device 103 is propelled. In concrete terms, the device 102 external to the living body transmits a command from the wireless transmission and reception section 105 to urge electrical stimulation, and, upon receipt of this command, the capsule type medical device 103 flows electric current from the plus electrodes 142$a$ through 142$f$ via the living body tissue to the minus electrodes 144$a$ through 144$f$, thus applying an electrical stimulus to the living body tissue, so as to cause the luminar tissue to shrink.

When the capsule type medical device 103 flows the electric current in this manner, initially, it operates the sense of force sensor 127, and selects the plus electrodes 142a through 142f and the minus electrodes 144a through 144f through which the electric current is to flow. In other words, as shown in FIG. 18, the sense of force sensor 127 changes over the contact points of the switching circuits 151a, 15b, 151c, and 151d which are included in the switching circuit 151 for deformation gauging in order while maintaining synchrony between them, and acquires change of the resistance value of the bridge circuits 149a through 149f which consist of the deformation gauges 145a through 145f, 146a through 146f, 147a through 147f, and 148a through 148f as voltage, which it converts into contact pressure with the voltage load transducer 154.

The contract pressure which has been detected in this manner is inputted to the control circuit 129. In the control circuit 129, it is determined whether or not the contact pressure which has been detected by the sense of force sensor 127 exceeds a predetermined value which is set in advance.

If the contact pressure is smaller than the predetermined value, then the control circuit 129 decides whether one or more of each of the electrodes 142 and 144 on the plus side and on the minus side is not effectively in contact with living body tissue, and it continues the monitoring of the contact pressure until one of more of each of the electrodes 142 and 144 comes to be in a contacting state. It should be understood that this monitoring of the contact pressure may be performed continuously, or may be performed intermittently.

On the other hand, if the contact pressure which has been detected by the sense of force sensor 127 is greater than or equal to the predetermined value, then it is decided that the electrodes 142a through 142f and 144a through 144f which are fitted to its bridge circuit 149a through 149f are sufficiently in contact with living body tissue, and it is decided that it is possible to flow electric current from these electrodes 142a through 142f and 144a through 144f to living body tissue.

If it has been decided that one or more of the electrodes 142 and 144 on each of the plus side and the minus side is effectively in contact, then the control circuit 129 changes over the switching element 141 of the plus electrode portion 125, and connects the plus electrode 142a through 142f for which the predetermined contact pressure is obtained to the current generation device 124. Furthermore, it changes over the switching element 143 of the minus electrode portion 126, and connects the minus electrode 144a through 144f for which the predetermined contact pressure is obtained to the ground of the other circuits within the capsule type medical device 102. It should be understood that, in FIG. 16, the situation is shown in which the switching elements 141 and 143 are set so that the electric current flows from the plus electrode 142f to the minus electrode 144c.

Next, the control circuit 129 sets the oscillation waveform of the oscillator 136 of the current generation device 124 and the gain of the gain adjustment circuit 137. Although it will be acceptable for the value of the gain which is set to be a value which is set in advance, it would also be acceptable to set the gain by inferring the contact impedance from the contact pressures between the electrodes 142 and 144 which are selected and living body tissue. In this case, if the contact pressure is greater, the gain is set to be smaller, since the contact impedance is smaller. Moreover, if the contact pressure is smaller, the gain is set to be greater, since the contact impedance is greater. Furthermore, it is possible to apply a stabilized electric current to the living body tissue, by monitoring the value of the electric current sensor 140 when the electric current is flowing through the living body tissue, and by feeding it back to the setting of the gain of the gain adjustment circuit 137.

When the above described setting has been completed, the control circuit 129 supplies the electric current which is generated by the current generation device 124 to the plus electrode portion 125. In concrete terms, it operates the oscillator 136 and generates a signal of the predetermined waveform, amplifies this signal with the gain adjustment circuit 137, and converts it into electric current with the driver 138. It supplies this electric current via the electric current sensor to the plus electrode portion 125, and flows this electric current via the living body tissue between the plus electrode 142 and the minus electrode 144.

Thus, an electric current signal according to the voltage waveform of the oscillator 136 is applied to the living body tissue, the luminal tissue shrinks. Since this shrinkage operation acts so as to push out the inclined surface of the rear portion 156 (refer to FIG. 18) of the capsule 121 upon which the electrodes 142 and 144 are arranged, thereby the capsule type medical device 103 is caused to be propelled with its tip portion 155 on the forward side. When the capsule type medical device 103 is thus caused continually to advance, it will be acceptable to continue to flow the electric current to the same plus electrode 142 and minus electrode 144, or to detect the contact pressure with the sense of force sensor 127, to select in order the most suitable combination of the electrodes 142 and 144, and to flow the electric current to them.

Figure 21:
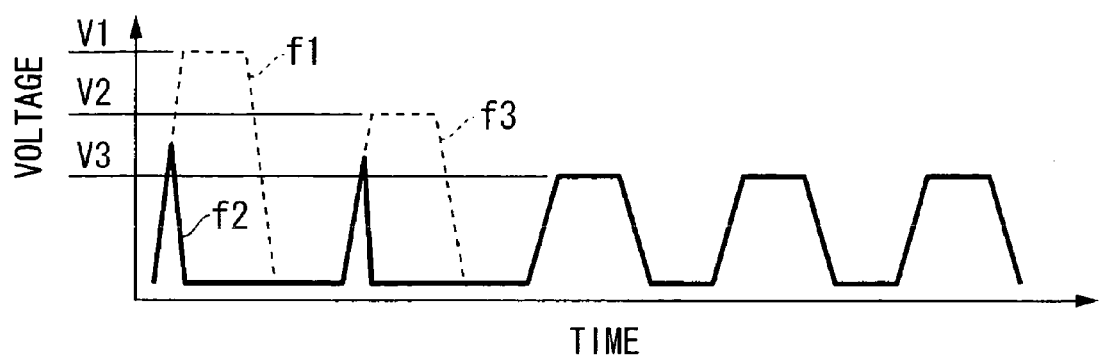
FIG. 21 is a figure showing the change with time of a voltage waveform which is output from a gain adjustment circuit.

The control of the electric current for the current generation device 124 will now be explained using FIG. 15 and FIG. 21. FIG. 21 shows the change of the voltage waveform which is outputted from the gain adjustment circuit.

Initially, the oscillator 136 generates a trapezoidal wave, and this trapezoidal wave is amplified by the gain adjustment circuit 137 by a gain which is set in advance; for example, as shown in FIG. 21, a voltage waveform f1 may be outputted of which the maximum voltage is V1. This voltage waveform f1 is converted by the driver 138 into an electric current value, and this electric current which has been obtained by conversion is flowed, via the resistor 139 and the electric current sensor 140, to the living body tissue from the plus electrode portion 125, and recirculates from the electric current section 126.

At this time, the control circuit 129 monitors the value of the electric current sensor 140, so as not to apply an electric current of greater than or equal to a predetermined electric current value IL to the living body tissue. If the electric current value is less than or equal to IL, then it continues to flow an the electric current according to the voltage waveform f1. On the other hand, if the electric current value is greater than IL, then either it stops the oscillator 136, or it lowers the gain of the gain adjustment circuit 137, or performs both these actions, so that, during this period, the application of the electrical stimulus is stopped therefore, the waveform of the output voltage in this type of case comes to be like the voltage waveform f2 shown by the solid lines.

Next, the control circuit 129 sets the gain so that the voltage waveform which is outputted from the gain adjustment circuit 137 becomes the voltage V2 which is lower than the voltage V1, like the voltage waveform f3. The value of the voltage V2 may be set in advance, or may be inferred by the control circuit 129 from the time period from when the electric current corresponding to the voltage V1 is applied to the living body, until the electric current value IL is exceeded. If, even though the gain is reduced in this manner, the electric current value IL is exceeded, then, after the output waveform becomes like the voltage waveform f2 again, the above described procedure is repeated.

In other words, the control circuit 129 sets the gain so that the voltage waveform which is outputted from the gain adjustment circuit 137 becomes a voltage V3 which is less than the voltage V2. If, with this gain, the electric current becomes less than the electric current value IL, then it continues to supply the electric current with this gain. Since, by controlling the gain by doing this, it is possible to limit the electric current and to apply an appropriate electrical stimulus to the living body, accordingly it is possible to obtain a propulsive force for the capsule type medical device in a stable manner.

It should be understood that since, with this type of control, it never happens that an electric current of greater than the electric current value IL which is set in advance comes to be applied to the living body, accordingly it would be possible to omit the resistor 139.

Furthermore, in order to perform the control of the electric current with good responsiveness, it would also be possible to employ a structure in which a limit value for the value of the electric current sensor 140 is decided by a comparator or the like (not shown in the drawings), and which stop to output it directly.

Since, according to this first variant example, it has been arranged to include the plurality of electrodes 142a through 142f and 144a through 144f, and to flow the electric current after checking the contact state between the living body tissue and the electrodes 142a through 142f and 144a through 144f with the sense of force sensor 127, accordingly it becomes possible to flow the electrical current in a stabilized manner. Moreover, it becomes possible to flow the electric current to living body tissue reliably. Accordingly, it becomes possible to stabilize the propulsion of the capsule type medical device. Since it is arranged to provide the electrodes 142a through 142f and 144a through 144f in plurality, and to switch between the plurality of electrodes 142a through 142f and 144a through 144f in order, so as to select the electrode through which to flow the electric current, accordingly, it becomes easy to apply an electrical stimulus to the body and to stabilize the capsule type medical device, and moreover it is possible to propel it reliably.

Furthermore, by adjusting the gain by feeding back the electric current value, it is possible to limit the electric current value to less than or equal to a predetermined value. Accordingly, it is possible to apply the electrical stimulus to the living body tissue in a stabilized manner. Moreover, it is possible to lengthen the life of the battery 130.

Thus, since it is possible to apply the electrical stimulus to the living body tissue in correspondence with the site within the living body which is obtained with the first embodiment, along with the beneficial effect that it is possible to perform observation with good efficiency, it is also possible to obtain the beneficial effects as described above.

Figure 22:
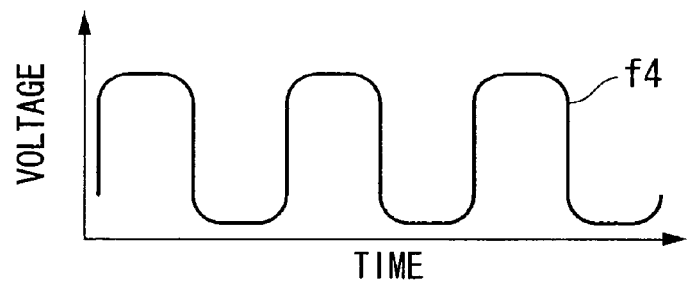
FIG. 22 is a figure showing the change with time of the voltage waveform which is output from the gain adjustment circuit.

It should be understood that it would also be acceptable to gently deform the edge portions of the voltage waveform which is outputted from the gain adjustment circuit 137, like the voltage waveform f4 shown in FIG. 22, so that its corners are made like a round square wave. Since, by making its edge portions from a square wave, the high frequency component is no longer generated when this type of voltage waveform is utilized, therefore the application of unintentional high frequency electric currents is eliminated. Accordingly, it is possible to apply the electrical stimulus in a stabilized manner.

Figure 23:
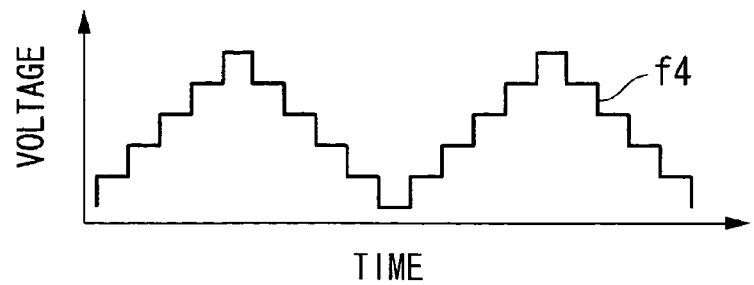
FIG. 23 is a figure showing the change with time of the voltage waveform which is output from the gain adjustment circuit.

Furthermore, it would also be acceptable to form the voltage waveform which is outputted from the gain adjustment circuit 137 as a triangular waveform such as one which rises and falls in a step form, like the voltage waveform shown in FIG. 23. Since, by utilizing this type of waveform, even though a high frequency component is generated, it is possible to make its power low, therefore it is possible to prevent electric currents of an unintentionally high frequency from being applied to the living body tissue at a strength greater than intended. Accordingly, it is possible to apply the electrical stimulus in a stabilized manner.

Next, a second variant example of the first embodiment of the capsule type medical device system of the present invention will be explained in detail with reference to the drawings. It should be understood that, to structural elements which are the same as in the first variant example, the same reference symbols are affixed, and overlapped explanation is omitted.

In the capsule type medical device according to this second variant example, its elongated capsule has a long and thin shape along its direction of advance and retreat, and it is characterized in that a plurality of electrodes are arranged along its longitudinal direction in a number of stages.

Figure 24:
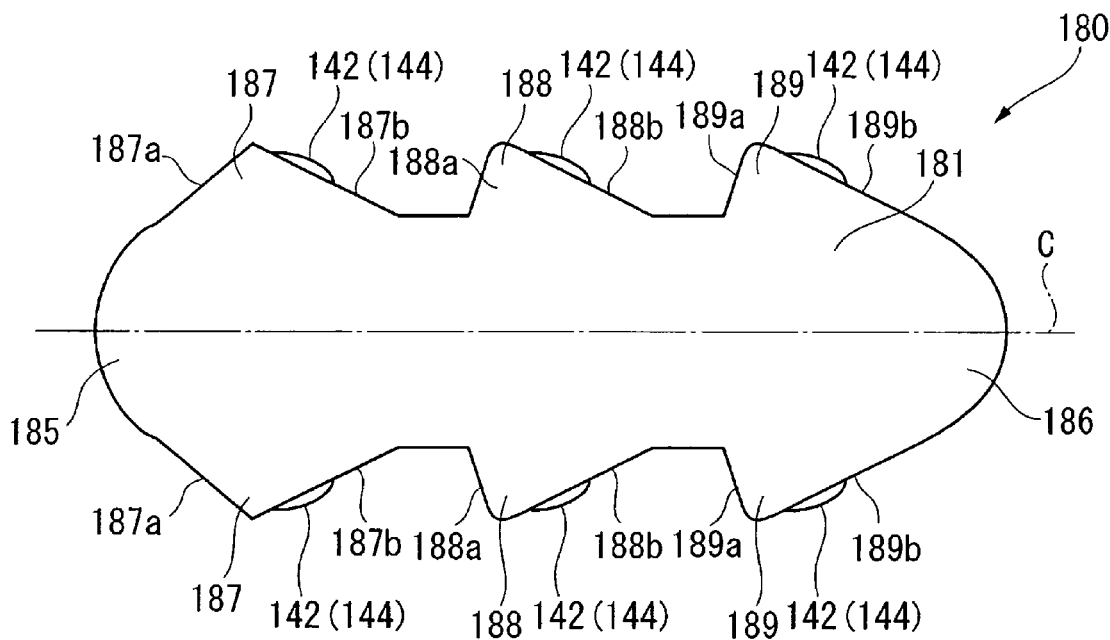
FIG. 24 is an external view showing a second variant example of the capsule type medical device system according to the first embodiment of the present invention.

As shown in FIG. 24, on the side surface of the capsule 181 of this capsule type medical device 180, from its tip portion 185 to its rear portion 186, along the longitudinal direction (its central axis C in FIG. 24), there are formed three projecting portions 187, 188, and 189 in a symmetrical saw-tooth wave shape with respect to the central axis C. From their most projected portions, these projecting portions 187, 188, and 189 have inclined portions 187a, 188a, and 189a which slope towards the tip portion 185, and inclined portions 187b, 188b, and 189b which slope towards the rear portion 186. The slope of the inclined portions 187b, 188b, and 189b is gentler than that of the inclined portions 187a, 188a, and 189a, so that, relatively, they can contact against living body tissue more easily. Furthermore, upon each of these inclined portions 187b, 188b, and 189b, there is provided a plus electrode 142 and a minus electrode 144. At least one group of a plus electrode 142 and a minus electrode 144 are provided upon each single projecting portion 187, 188, and 189.

This capsule type medical device 180 uses a sense of force sensor as shown in FIG. 18, which detects the contact pressure against living body tissue of the plus electrodes and the minus electrodes which are provided to each of the projecting portions 187, 188, and 189. A plus electrode 142 and a minus electrode 144 which have a predetermined contact pressure are selected by the control circuit 129, and electrical stimulation is applied to the living body tissue thereby. The electrical current at this time is controlled by using the gain adjustment circuit and so on.

According to this second variant example, it is possible to obtain the same beneficial effects as with the first variant example of the first embodiment. Furthermore, it is possible to increase the number of locations at which electrical stimulation can be applied to living body tissue, since, upon the outer periphery of a cross section orthogonal to the longitudinal direction of the capsule 181, the first stage electrodes 142 and 144 are positioned upon the projecting portion 187 towards the tip portion 185, the second stage electrodes 142 and 144 are positioned upon the projecting portion 188 more to the rear portion 186 than the projecting portion 188, and the third stage electrodes 142 and 144 are positioned upon the projecting portion 189 towards the rearmost portion 186. Accordingly, it is possible to propel this capsule type medical device 180 with good efficiency.

It should be understood that although, in FIG. 24, a structure is shown in which the electrodes 142 and 144 are arranged in multiple stages on both side surfaces of the capsule 181 of the capsule type medical device 180, if the projecting portions 187, 188, and 189 are provided so as to surround the outer periphery of the cross section orthogonal to the longitudinal direction of the capsule 181, it would also be possible to arrange a greater number of the plus electrodes 142 and the minus electrodes 144.

Yet further, it would also be acceptable to arrange to select one group each of the electrodes 142 and 144 from each of the projecting portions 187, 188, and 189, and, at a maximum, to flow electric current via living body tissue between these three groups of plus electrodes 142 and minus electrodes 144.

Next, a third variant example of the first embodiment of the capsule type medical device system of the present invention will be explained in detail with reference to the drawings. It should be understood that, to structural elements which are the same as in the first and second variant examples, the same reference symbols are affixed, and overlapped explanation is omitted.

This third variant example is characterized in that the electrodes are arranged so as to be able to propel the capsule type medical device both forwards and backwards.

Figure 25:
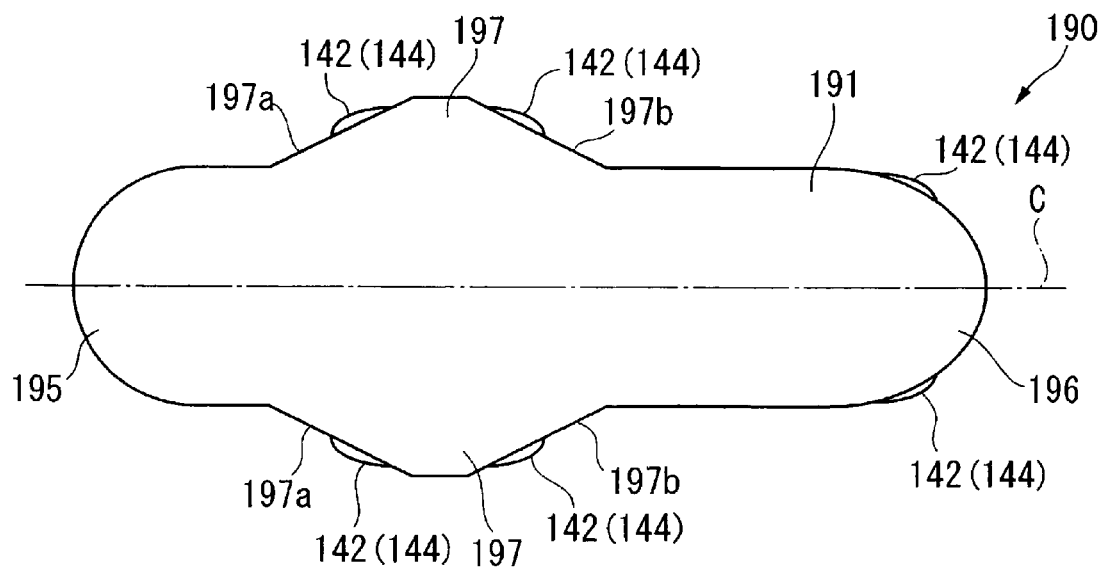
FIG. 25 is an external view showing a third variant example of the capsule type medical device system according to the first embodiment of the present invention.

As shown in FIG. 25, the capsule 191 of this capsule type medical device 190 has a large diameter portion 197 between from its tip portion 195 to its rear portion 196, such that its outer diameter increases in the direction which is roughly orthogonal to the central axis C along the longitudinal direction of the long and thin capsule 191. This large diameter portion 197 has an inclined portion 197*a* which slopes towards the tip portion 195, and an inclined portion 197*b* which slopes toward the rear portion 196; and, upon each of these inclined portions 197*a* and 197*b*, there is provided at least one group of a plus electrode 142 and a minus electrode 144. Furthermore, upon the rear portion 196 of the capsule 191 as well, there is provided at least one group of a plus electrode 142 and a minus electrode 144.

The ends of the electrodes 142 and 144 project towards the living body tissue from the capsule 191. The electrodes 142 and 144 which are disposed upon the inclined portion 197*a* project towards the direction of progress (i.e. towards the tip portion 195). And the electrodes 142 and 144 which are disposed upon the inclined portion 197*b* project towards the direction which is opposite to the direction of progress (i.e. towards the rear portion 196). The plus electrodes which are arranged in this manner, constitute the plus electrode portion 125, as shown in FIG. 16, and are connected to the current generation device 124 (refer to FIG. 15).

The switching element 141 may be made so as to change over the electrical conduction state of all of the plus electrodes 142. Furthermore, the switching element which changes over the plus electrodes which are disposed upon the inclined portion 197*a*, and the switching element which changes over the plus electrodes 142 which are disposed upon the inclined portion 197*b* and upon the rear portion 196, are constituted separately, and, for each of these switching elements, it will be acceptable to change over the plus electrodes 142 independently. The same holds for the minus electrodes 144.

Next, the operation of this capsule type medical device 190 will be explained.

If the tip portion 195 is oriented in the direction of progression, when the capsule type medical device 190 is to be caused to advance, the contact pressure against living body tissue is detected from the electrodes 142 and 144 of the inclined portion 197*b* and the electrodes 142 and 144 of the rear portion 196. Electric current is supplied to the plus electrodes 142 and the minus electrodes 144 which have been selected by the control circuit 129 based upon the contact pressure, so that an electrical stimulus is applied to the living body tissue. On the other hand, when the capsule type medical device 190 is to be caused to retreat, then electric current is flowed via the living body tissue to the plus electrodes 142 and the minus electrodes 144 which are selected from among the electrodes 142 and 144 upon the inclined portion 197*a*, based upon the contact pressure.

Furthermore, if the tip portion 195 is oriented in the opposite direction to the direction of progress, while the rear portion 196 is oriented in the direction of progress, then, when advancing, electrodes are utilized which have been selected from the electrodes 142 and 144 upon the inclined portion 197*b* and from the electrodes 142 and 144 upon the rear portion 196; while, when retreating, electrodes are utilized which have been selected from the electrodes 142 and 144 upon the inclined portion 197*a*.

According to this third variant example, it is possible to obtain the same beneficial effects as with the first and second variant examples. Furthermore, by selecting the electrodes to which to supply electrical power, it is possible to change over the direction of progress of the capsule type medical device 190 by electrical stimulation.

It should be understood that the present invention is not limited to these various embodiments; it can be applied widely. For example, instead of selecting the electrodes 142 and 144 with the sense of force sensor 127, it would also be acceptable to select the electrodes 142 and 144 by using a voltage meter which is provided between the input sides of the plus electrode portions 125 and the output sides of the minus electrode portions 126. In concrete terms, it will be acceptable, while switching over the electrodes 142 and 144, to apply a very weak electric current to the living body tissue from the current generation device and to measure the voltage between the plus electrode 142 which has been selected and the minus electrode 144 which has been selected, with the control circuit 129 calculating the impedance between the electrodes and selecting electrodes 142 and 144 like those for which the impedance is below a predetermined value to apply the electrical stimulus. The same beneficial effects may be obtained when measuring the impedance, by applying a fixed voltage, and by measuring the electric current value which flows at this time between the electrodes 142 and 144.

Furthermore, although the movement of the capsule type medical device 103, 180, or 190 is inferred according to change of the images taken by the CCD 134, it would also be acceptable to provide an acceleration sensor to the capsule type medical device 103, 180, or 190 (more desirably, a three dimensional acceleration sensor), and to determine that the position of the capsule type medical device 103, 180, or 190 has not changed if no acceleration has been detected over a long time period, and to perform control so as to shift over to the procedure of applying an electrical stimulus. In this case there is the beneficial effect that the control becomes convenient and simple, since the movement of the capsule type medical device 103, 180, or 190 is detected only by the output of the acceleration sensor, and accordingly there is no requirement for any decision as to the requirement or otherwise for application of electrical stimulation to be made according to the performance of communication with the device 102 external to the living body. It should be understood that, instead of the acceleration sensor, it would also be acceptable to utilize a speed sensor.

Yet further, it would also be acceptable to provide an acceleration sensor to the device 102 external to the living body as well, and to decide that the movement of the capsule type medical device 103, 180, or 190 with respect to the lumen has ceased when the difference has disappeared between the output values of the two acceleration sensors i.e., the difference between the output value of the sensor which is provided to the capsule type medical device 103, 180, or 190, and the output value of the sensor which is provided to the device 102 external to the living body. By doing this, even if the test subject has moved, it is possible to infer movement of the capsule type medical device 103, 180, or 190 with respect to the lumen by canceling out the operation thereof. It should be understood that the decision as to the presence or absence of shifting based upon the output of the acceleration sensor might be performed by the control circuit 129 of the capsule type medical device 103, 180, or 190, or might be performed by the control section 108 external to the living body of the device 102 external to the living body.

Next, with regard to the timing by which the imaging element 20 and the optical system 21 such as the LED or the like of the first embodiment of the capsule type medical device system of the present invention is caused to operate, a preferred example thereof will be explained in detail, as a fourth variant example of the first embodiment.

Figure 26:
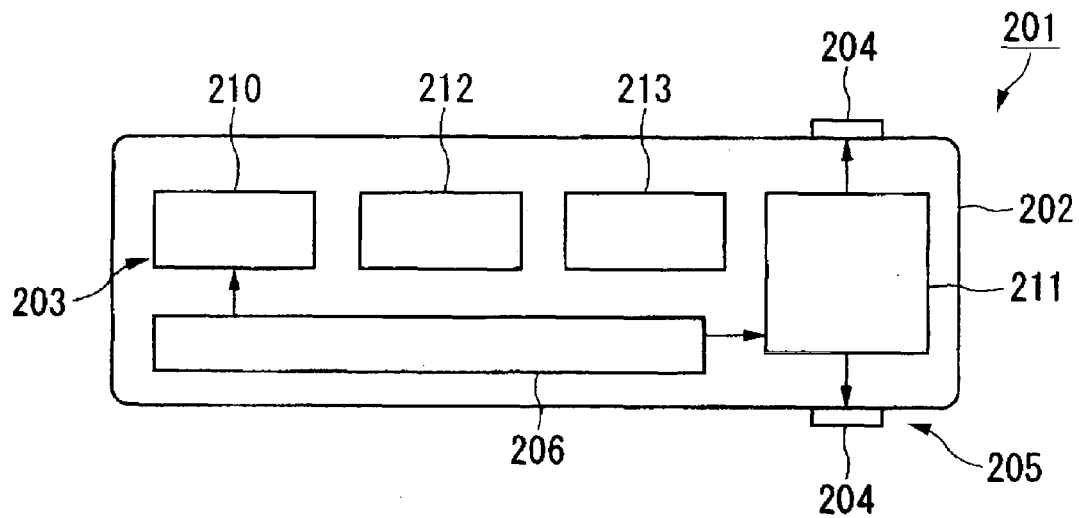
FIG. 26 is a structural diagram showing a fourth variant example of the capsule type medical device system according to the first embodiment of the present invention.

The capsule type medical device 201 of this fourth variant example, as shown in FIG. 26, includes: a capsule shaped casing 202; an imaging device 203 which takes images of the inside of the living body; an electrical stimulation device 205 which is provided upon the outer surface of the casing 202, and which includes electrodes 204 which apply electrical stimulation to living body tissue; and a timing controller (i.e. a control section) 206 which causes each of the imaging device 203 and the electrical stimulation device 205 to operate at its own different and separate timing.

The casing 202 is made from a plastic material or the like so as tightly to enclose its interior, and a transparent cover which is not shown in the figures is provided at one end thereof. At the inside of this transparent cover, there is disposed an optical system which consists of an imaging element not shown in the drawings which obtains images by the imaging device various portions of the inside of the living body, and a LED or the like which illuminates the visual range of this imaging element by emitting illumination light. Furthermore, the imaging element receives a signal from an imaging circuit 210 and is driven thereby. In other words, the imaging element and the imaging circuit 210 constitute an imaging device 203.

The electrodes 204 are provided as a pair at the one end of the casing 202, so as to sandwich the axial line of the casing 202, and, upon receipt of a signal from an electrical stimulation circuit 211, they are capable of flowing an electrical current to living body tissue and thus applying an electrical stimulus. These electrodes 204 and this electrical stimulation circuit 211 constitute the electrical stimulation device 205.

Furthermore, the electrodes 204 are transparent electrodes which are optically transparent. In other words, the electrodes 204 are made from transparent electrically conductive layers which have a combination of high transparency and electrical conductivity. Such a transparent electrically conductive layer, for example, may be made by forming, upon a glass substrate, a thin layer of tin oxide with a little added fluorine, or a thin layer of indium oxide with a little added ammonia.

Within the casing 202, there are provided a memory 212 which records the images of the inside of the living body which have been taken images by the imaging device 203, and a battery 213 which supplies electrical power to the various structural components.

Figure 27:
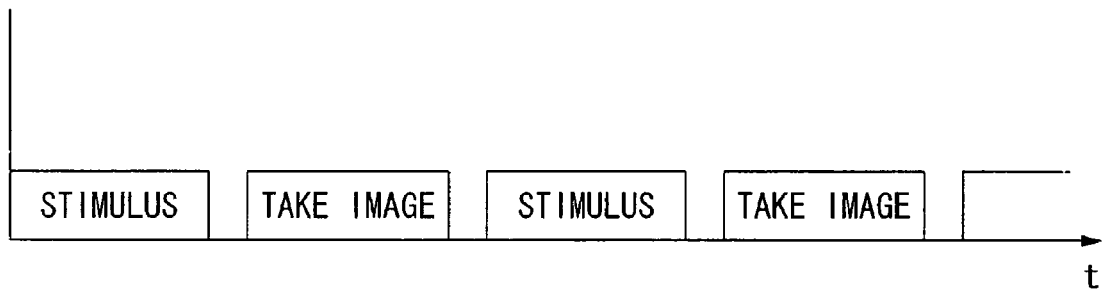
FIG. 27 is a view showing the operational timing of a timing controller of the capsule type medical device shown in FIG. 26.

As shown in FIG. 27, the timing controller 206 sets in advance the operating time periods so that the imaging device 203 and the electrical stimulation device 205 each operates individually and separately. By doing this, the operational timings are mutually displaced from one another. In other words, the timing controller 206 initially turns the imaging circuit 210 ON and acquires images; and thereafter it repeats the actions of: along with turning the imaging circuit 210 OFF, also turning the electrical stimulation circuit 211 ON and applying an electrical stimulus, and thereafter, along with turning the electrical stimulation circuit 211 OFF, also turning the imaging circuit 210 ON.

The case of taking an image of the interior of the body of a person who is the subject of investigation with a capsule type medical device 201 which has this type of structure will now be explained in the following.

When the capsule type medical device 201 is ingested by the person who is the subject of investigation into the interior of his body, a switch which is not shown in the figures comes to be turned ON, and electrical power is supplied from the battery 213 to the various structural components. therefore, as shown in FIG. 27, the timing controller 206 operates the imaging device 203 and the electrical stimulation device 205 at their individual separate timings. In other words, the timing controller 206 first operates the imaging circuit 210 and performs images of the inside of the living body with the imaging element. Images which are taken images are recorded in the memory 212. Next, at the same time as turning the imaging circuit 210 OFF, the timing controller 206 also operates the electrical stimulation circuit 211, and flows an electrical current so as to apply an electrical stimulus to the living body tissue from the electrodes 204. Therefore, the operation of shrinking the living body tissue of, for example, the small intestine or the like (the intestinal wall) is performed. By this shrinking of the living body tissue, the one end of the casing 202 of the capsule type medical device 201 is pushed out by the living body tissue, so that it shifts within the alimentary canal.

After the shifting, at the same time as turning the electrical stimulation circuit OFF, the timing controller 206 causes the imaging circuit 210 to operate, and thereby performs images of the inside of the living body for a second time.

According to this fourth variant example, since the timing controller 206 operates the imaging device 203 and the electrical stimulation device 205 at their individual different timings, images are not acquired while applying electrical stimulation to the living body tissue. In other words, since an image is performed only in the state of reliably being stopped, or, in detail, when shifting at a slow speed such as due to peristaltic movement of the small intestine or the like, accordingly it is possible to acquire desirable images which have no blurring or the like. Accordingly, after this, when detecting the state of health of the person who is the subject of investigation based upon images which are recorded in the memory 212, it is possible to enhance the reliability thereof.

Furthermore, since the electrodes 204 are transparent electrodes, the imaging device 203 is able to obtain proper images accurately, irrespective of the positions in which these electrodes 204 are arranged. Therefore, since there is no limitation imposed upon the positions for arrangement of the electrodes 204, the freedom of design is enhanced.

Accordingly, since it is possible to apply an electrical stimulus to the living body tissue in correspondence with the site within the living body which is obtained by the first embodiment, along with the beneficial effect that it is possible to perform observation with good efficiency, it is also possible to obtain the beneficial effects as described above.

Next, a fifth variant example of the first embodiment of the capsule type medical device system of the present invention will be explained in detail with reference to the drawings. It should be understood that, to structural elements which are the same as in the fourth variant example, the same reference symbols are affixed, and overlapped explanation is omitted.

In the fourth variant example, the timing controller 206 itself within the casing 202 controls the imaging device 203 and the electrical stimulation device 205. By contrast to this, in this fifth variant example, the timing controller 206 operates based upon a control signal from outside the living body.

Figure 28:
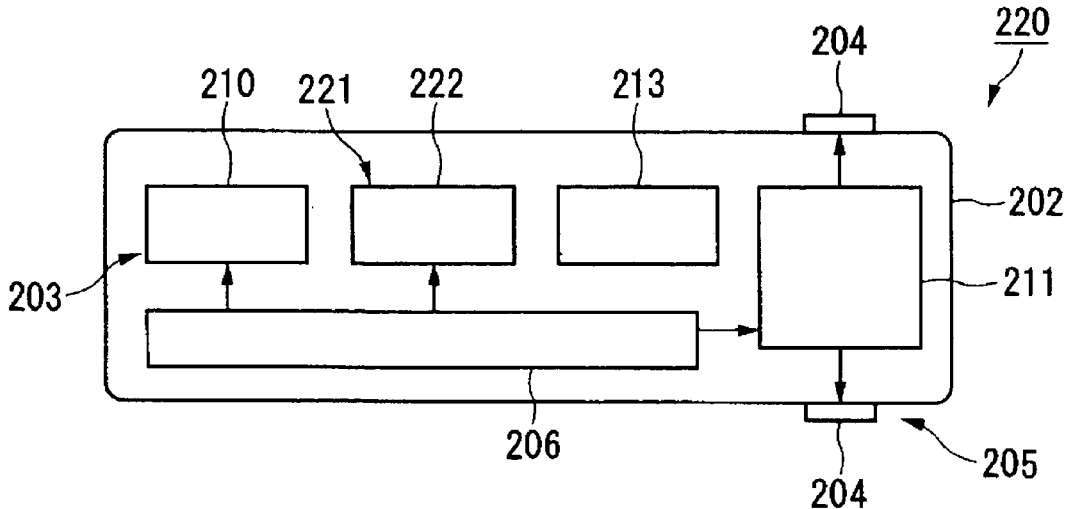
FIG. 28 is a structural diagram showing a fifth variant example of the capsule type medical device system according to the first embodiment of the present invention.

In other words, as shown in FIG. 28, the capsule type medical device 220 of this fifth variant example includes, within its casing 202, a wireless transmission device 221 which wirelessly transmits by radio waves the above described control signal between itself and an external device not shown in the drawings, which is disposed externally to the living body, and the timing controller 206 operates based upon this control signal.

The wireless transmission device 221 includes a wireless transmission circuit 222 and a signal transmission and reception antenna which is not shown in the figures, and it transmits the control signal which it has received to the timing controller 206.

According to the capsule type medical device 220 which has this type of structure, by sending the control signal from the external device, it is possible to control the operation of the imaging device 203 and of the electrical stimulation device 205 easily and moreover accurately. At this time, the time period at which the control signal is sent may be the same time period as the time period that the imaging circuit 210 or the electrical stimulation circuit 11 is ON, or may be different. In particular, since no complicated circuitry and so on is required to be provided for the timing controller 206, it is possible to anticipate a reduction in the cost for the components, and it is also possible to anticipate a reduction in the size of the capsule type medical device 201.

It should be understood that, in this fifth variant example, the images which are taken images by the imaging device 203 may not be recorded in any memory 212; rather, it may be set so that they are transmitted via the wireless transmission device 221 to the external device. By doing this, it is possible to check the state of health of the person who is the subject of investigation with the external device quickly. Furthermore, this example is not limited to the use of radio waves; it would also be possible to control the timing controller 206 by some other type of control signal, such as by a magnetic field or the like.

Next, a sixth variant example of the first embodiment of the capsule type medical device system of the present invention will be explained in detail with reference to the drawings. It should be understood that, to structural elements which are the same as in the fifth variant example, the same reference symbols are affixed, and overlapped explanation is omitted.

Figure 29:
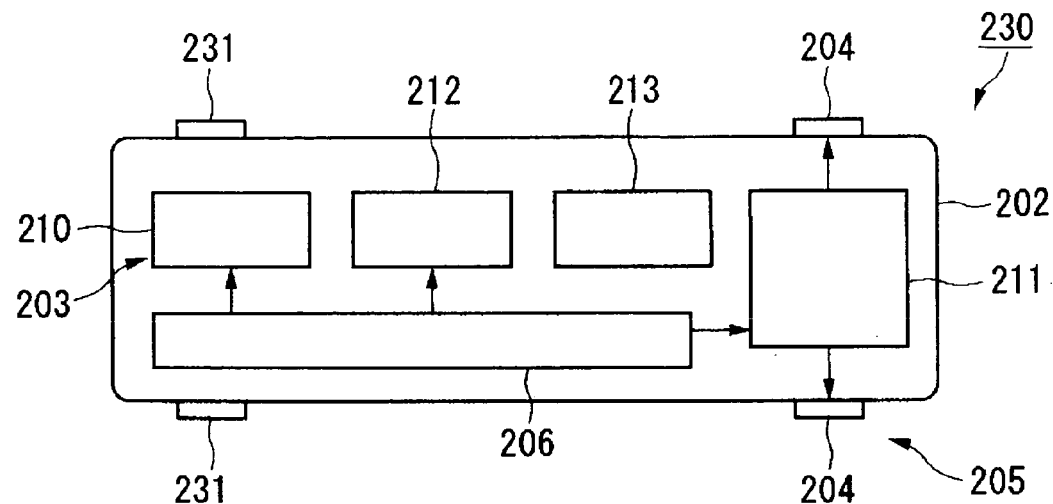
FIG. 29 is a structural diagram showing a sixth variant example of the capsule type medical device system according to the first embodiment of the present invention.
Figure 30:
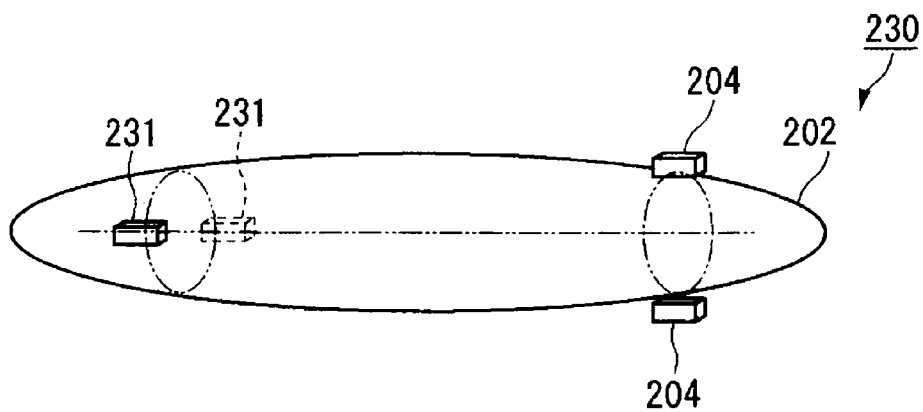
FIG. 30 is an external view of the capsule type medical device shown in FIG. 29, and is a figure showing the positional relationship of the electrodes.

In the fifth variant example, upon receipt of a control signal from the external device, the timing controller 206 within the casing 202 operated at a different operational timing from the imaging device 203 and the electrical stimulation device 205. By contrast to this, in this sixth variant example, the timing controller 206 is caused to operate simultaneously with the imaging device 203 and the electrical stimulation device 205, and takes images of the living body tissue in the state in which it is being held in position at the location which is taken images. In other words, as shown in FIG. 29, the capsule type medical device 230 of this sixth variant example has, in addition to the electrodes 204 which are provided at its one end, furthermore, electrodes 231 which are provided as a pair at the other end of the casing 202, so as to sandwich the axial line of the casing 202. Furthermore, as shown in FIG. 30, the pair of electrodes 204 at the one end of the casing are disposed in positions which are rotated, with respect to the pair of electrodes 231 at the other end thereof, by approximately 90° around the axial line as a central axis. It should be understood that the electrodes 231 at this other end of the casing are transparent electrodes, just like the electrodes 204 at the one end of the casing. Furthermore, as described above, the timing controller 206 operates at the same timing, as do the imaging device 203 and the electrical stimulation device 205.

Since, according to the capsule type medical device 230 which is structured in this manner, the electrodes 204 at the one end or the electrodes 231 at the other end are positioned towards the front or towards the back in the direction of progress, therefore, when an electrical stimulus is applied to the living body tissue, the living body tissue shrinks so as to block the forward or reverse direction of the casing 202. Therefore, the capsule type medical device 201 does not move in either the forward or the backward direction, and comes to be in the state of staying in the same position. In other words, the living body tissue operates to close the lumen at the positions before and after the casing 202, and comes to be in the state of moving in closely so as to adhere closely to the outer surface of the casing 202.

The timing controller 206 causes the imaging device 203 to operate at the same time, thus performing images of the living body tissue which has shifted and moved in closely so as to adhere closely to the outer surface of the casing 202. Accordingly, the imaging device 203 can perform images in the state in which the location which it is desired to take images has stopped, and in the state in which the living body tissue is close up, so that it is possible for it to obtain good images, with which there is no blurring. In particular, since the image is performed in a state in which the distance between the imaging device 203 and the living body tissue is kept constant, for example, an image is performed while eliminating the influences of loss of dark detail and white-out and the like. Furthermore, it is easy to see any lesion in the small intestine or the like, since the image is performed in a state in which the folded living body tissue is stretched out.

Yet further, since the electrodes 204 at the one end and the electrodes 231 at the other end are offset by being rotated about 90°, taking the axial line as a center line, therefore, when applying an electrical stimulus to the living body tissue, it is possible to apply the electrical stimulus with good efficiency to the living body tissue while alleviating their mutual influence. Accordingly, it is possible to cause the shrinkage operation to be performed upon the living body tissue more reliably.

It should be understood that, with this sixth variant example, the imaging element of the imaging device 203 may also be provided on the side surface of the casing 202, so as to be positioned between the electrodes 204 at the one end and the electrodes 231 at the other end. By doing this, it is possible to take images of the living body tissue more appropriately.

Next, a seventh variant example of the first embodiment of the capsule type medical device system of the present invention will be explained in detail with reference to the drawings. It should be understood that, to structural elements which are the same as in the fifth variant example, the same reference symbols are affixed, and overlapped explanation is omitted.

In the fifth variant example, the timing controller 206 within the casing 202 caused the imaging device 203 and the electrical stimulation device 205 to operate at different operational timings, upon receipt of a control signal from the external device. By contrast to this, in this seventh variant example, after having operated the electrical stimulation device 205, the timing controller 206 operates the imaging device 203 after a predetermined time interval has elapsed.

Figure 31:
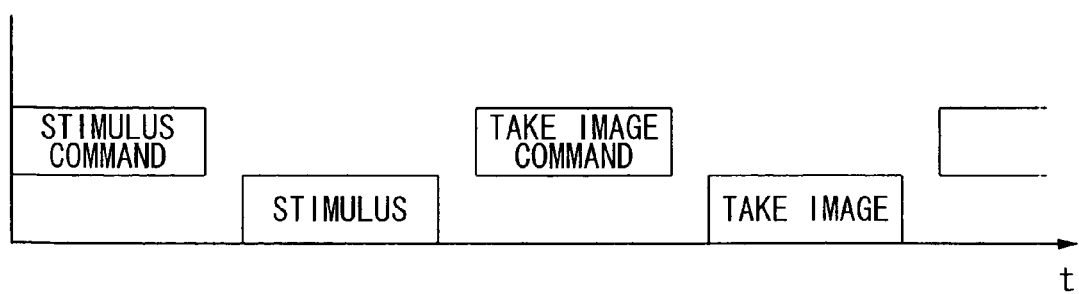
FIG. 31 is a view showing a seventh variant example of the capsule type medical device system according to the first embodiment of the present invention, and is a figure showing the operation timing of a timing controller.

As shown in FIG. 31, in this seventh variant example, after having applied an electrical stimulus to the living body tissue with the electrical stimulation device 203, the timing controller 206 causes the imaging device 205 to operate after a predetermined time interval has elapsed, in other words after the capsule has shifted along the direction of progress or backwards against the direction of progress. Accordingly, it is possible to obtain a desirable image without any blurring or the like, since the image is performed after performing shifting via the operation of shrinking the living body tissue. In particular, by adjusting the predetermined time period, it is possible to perform images in a state in which the living body tissue which is shrunk down has returned to its normal state, in other words, with the lumen, which had been blocked up, again having opened up.

It should be understood that, in this embodiment, it would also be acceptable to provide the electrodes at both ends of the casing 202, as in the above described sixth variant example. Furthermore, with the sixth variant example and the seventh variant example, it would be acceptable not to provide any wireless transmission device, and not to perform any wireless transmission with any external device, just as in the fourth variant example. Yet further, in the fourth variant example, it would be acceptable to provide the electrodes at both ends of the casing, just as in the sixth variant example.

Next, a second embodiment of the capsule type medical device system of the present invention will be explained with reference to FIG. 32. It should be understood that, to structural elements which have already been explained for the first embodiment, the same reference symbols are affixed, and explanation thereof is omitted.

Figure 33:
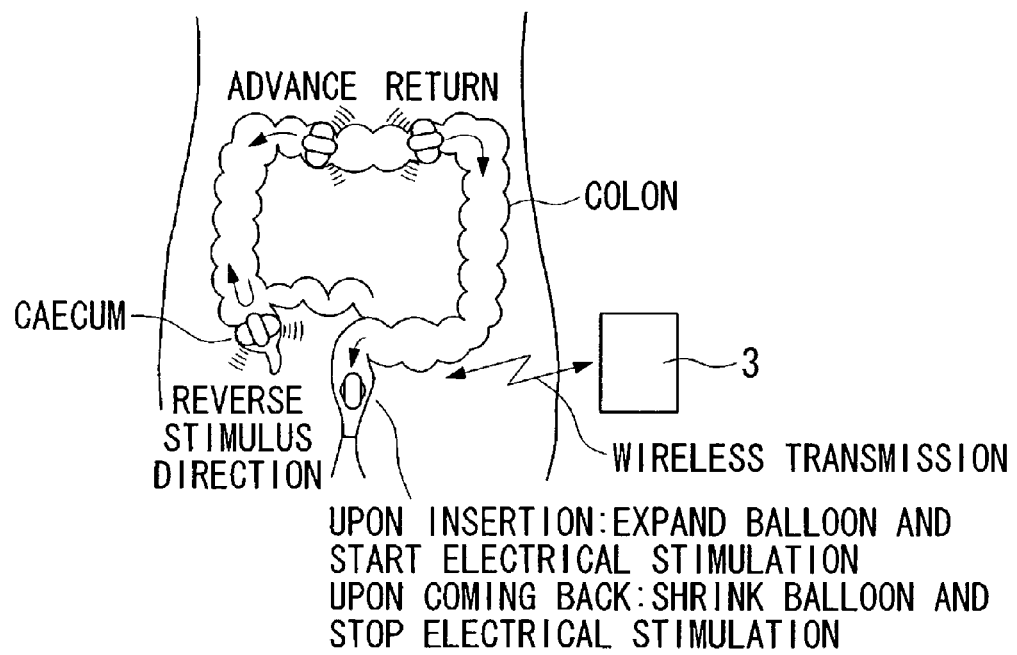
FIG. 33 is a figure showing a situation in which, after the capsule type medical device has been inserted into the colon via the anus, and has shifted up to the caecum, it is observing within the colon while shifting back to the anus again.

In this second embodiment, the various internal organs of the patient are observed from the ingestion of the capsule type medical device by mouth until it is excreted. By contrast to this, with the first embodiment, as shown in FIG. 33, the capsule type medical device 2 is ingested from the anus, and performs observation within the colon. At this time, it is ingested into the living body with the imaging element facing forwards. Upon ingestion, the capsule type medical device 2 transmits the images of the colon which have been taken images by the imaging element 20 to the external device 3. Upon receipt thereof, the position detection circuit 4 of the external device 3 detects that the capsule type medical device 2 is positioned within the colon, and the control section 33 transmits a control signal to the capsule type medical device 2 to expand the balloon 13 and to apply an electrical stimulus. Upon receipt of this control signal, the control section 6 of the capsule type medical device 2 causes the expansion and shrinkage mechanism 22 to operate, thus causing the balloon 13 to expand, and also applies an electrical stimulus to the living body tissue (the intestinal tract) by transmitting an electric current to the electrodes 5 from the current generation circuit 23. At this time, the current generation circuit 23 applies the electrical stimulus by supplying electric current to the electrodes 5 at the other end of the capsule.

The living body tissue which has received this electrical stimulus performs local shrinkage at the other end of the casing 10. Therefore, the capsule type medical device 2 performs images of the interior of the colon with the imaging element 20 while shifting within the colon so as to move backwards, from the anus towards the small intestine. When it arrives at the caecum, the control section 33 of the external device 3 sends a control signal to the capsule type medical device 2 to shrink down the balloon 13 and to stop the electrical stimulation.

Figure 32:
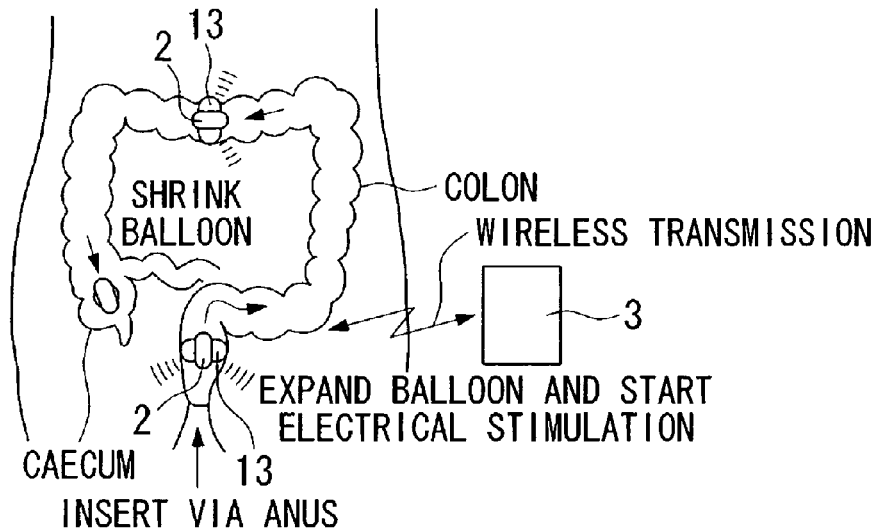
FIG. 32 is a view showing a second embodiment of the capsule type medical device system according to the present invention, and is a figure showing a situation in which the capsule type medical device has been inserted into the colon via the anus, and is observing up to the caecum.

Upon receipt of this signal, as shown in FIG. 32, the control section 6 of the capsule type medical device 2, along with causing the expansion and shrinkage mechanism 22 to operate and thus causing the balloon 13 to shrink, also stops the electric current which is being supplied to the electrodes 5, thus stopping the electrical stimulation. After this, the capsule type medical device 2 is excreted naturally. At this time its excretability is enhanced, since the balloon 13 is shrunk down.

According to this type of embodiment, it is possible to perform driving only within the colon, of which observation is required, so that it is possible to perform the observation more efficiently.

Furthermore, with the above described second embodiment, it is arranged that, when the capsule has arrived at the caecum, along with causing the balloon 13 to shrink down, the electrical stimulation is also stopped; but this is not to be considered as being limitative: for example, as shown in FIG. 33, it would also be acceptable to arrange matters so that, when the capsule has arrived at the caecum, the electrical stimulation from the electrodes 5 on the other end of the capsule is changed around for electrical stimulation from the electrodes 5 on the other end of the capsule. By doing this, it would be possible to cause the capsule type medical device 2, which had arrived at the caecum, to be shifted back towards the anus again due to electrical stimulation. It would be acceptable to arrange, when the capsule arrived at the anus, along with shrinking down the balloon 13, also to stop the electrical stimulation. By doing this, it would be possible to take images of the interior of the colon twice, while going up and while returning down, so that it would be possible to perform more accurate observation and to reduce oversights and the like. Furthermore, it would be possible to cause excretion at an early stage, since it would be possible to induce movement downwards to the anus.

It should be understood that although, in the above described embodiment, the electrodes are provided respectively at the one end and at the other end of the casing with respect to its axial direction, this should not be considered as being limitative; it would be acceptable for either one of these, only, to be provided; or, alternatively, a plurality could be provided. Furthermore although, in the above described embodiments, the electrodes are made as being provided upon the outer surface of the casing or upon the outer surface of the balloon, a structure would also be acceptable in which the electrodes are disposed in the vicinity of the outer surface of the casing, with the electrodes being covered over by an outer surface member which is made from a material which has high electrical conductivity. In this case, in order to prevent short circuiting from the plus poles to the minus poles over the outer surface of the casing, an insulating state should be established between the material which covers the positive poles and the material which covers the negative poles. By doing this, even if the electrodes are shaped to be very small, it is possible to perform electrical stimulation over a wide range of living body tissue via the members upon the outer surface of the casing.

Furthermore, it would also be acceptable to impart the functions with which the control section of the external device is equipped to the control section of the capsule type medical device. By doing this, it would be possible to change the wireless transmission between the capsule type medical device and the external device into one way communication (of in-vivo information) from the capsule type medical device to the external device.

Figure 34:
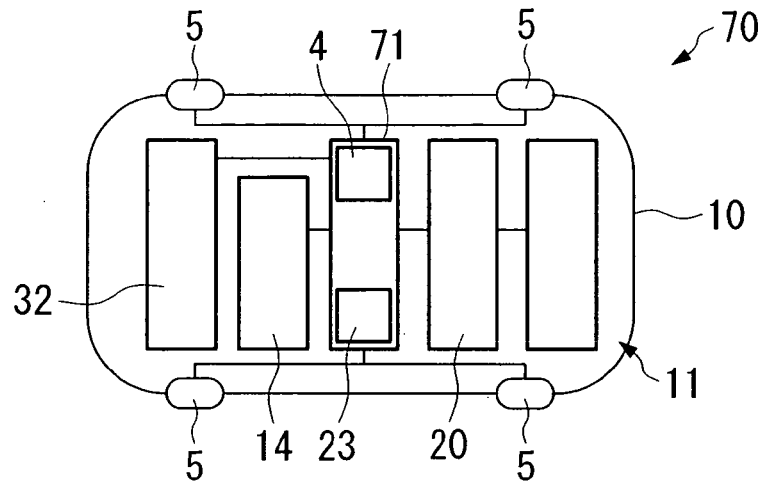
FIG. 34 is a sectional view showing an example of a capsule type medical device of the present invention.

Furthermore, it would also be acceptable to provide the recording device, not to the external device, but rather within the capsule type medical device. In other words, it would be acceptable to embody the present invention as the capsule type medical device shown in FIG. 34. Along with this capsule type medical device 70 including a recording device 32 within its casing 10, the control section 71 also includes a current generation circuit 23 and a position detection circuit 4. According to this capsule type medical device 70, when it is shifting within the living body, its own position is detected by the position detection circuit 4, while it is recording images which have been taken images by the imaging element 20, which are in-vivo information, in the recording device 32; and it is possible for the control section 71 to control the current generation circuit 23 according to the site at which it has arrived, so as to apply electrical stimulation. Accordingly, the operation is very simple and convenient, since the person who is the subject of investigation is not required to fit any external device.

It should be understood that, with this capsule type medical device as well, in the same manner as with the capsule type medical device systems described above, it would be acceptable also to provide a pH sensor or a balloon as well.

Figure 35:
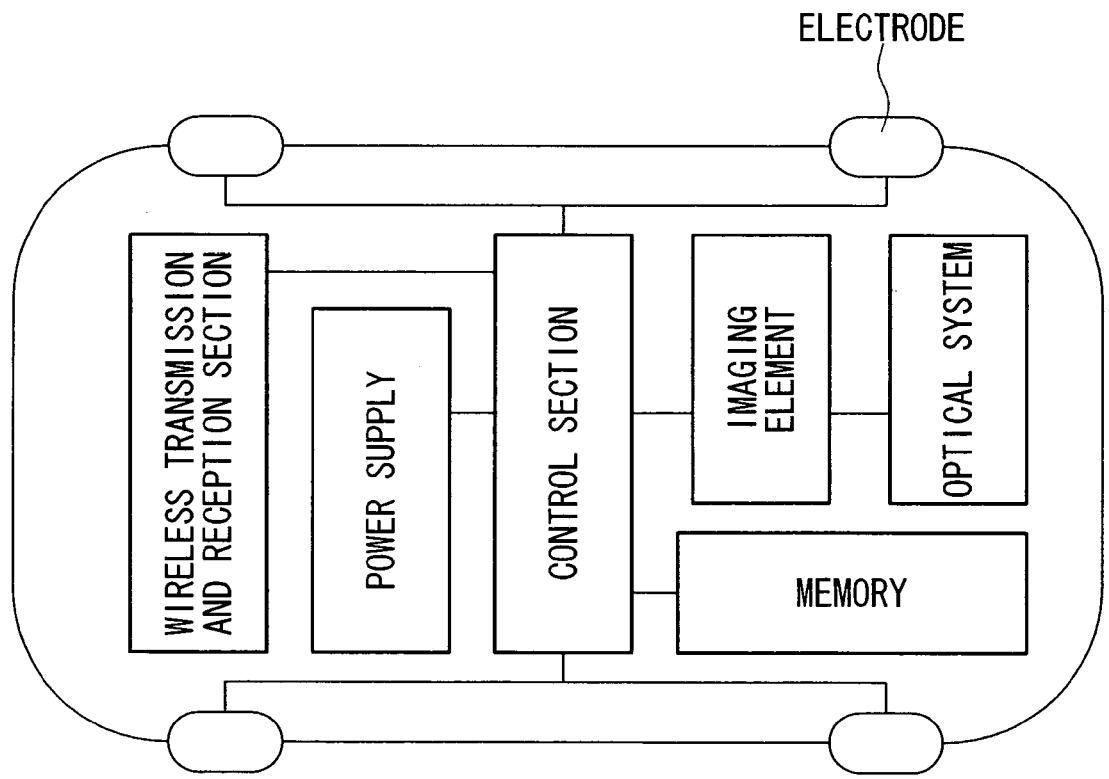
FIG. 35 is a sectional view showing another example of a capsule type medical device of the present invention.

Furthermore although, in the above described embodiments, a position detection device is provided for detecting the position of the capsule type medical device, it would also be acceptable, as shown in FIG. 35, for the position detection device to include a decision circuit not shown in the figure which is provided to the control section, and a decision device which includes a timer (a setting section) not shown in the figures, in which there is set in advance a parameter such as the time period which is required until the capsule arrives at the target site within the living body or the like.

This timer is set in advance to the time period from when the capsule is ingested into the living body until it arrives at a specified site. If this capsule type medical device is applied to the above described second embodiment, along with being able to decide, according to the time period of the timer, from when it is ingested into the living body via the anus to when it arrives at the caecum, it is also possible further to decide according to the time period of the timer, from when it is at the caecum to when it arrives back at the anus. According to the site within the living body which has been decided upon by the decision device, the control section may be set so as to perform expansion and shrinkage of the balloon, and performance of electrical stimulation.

Figure 36:
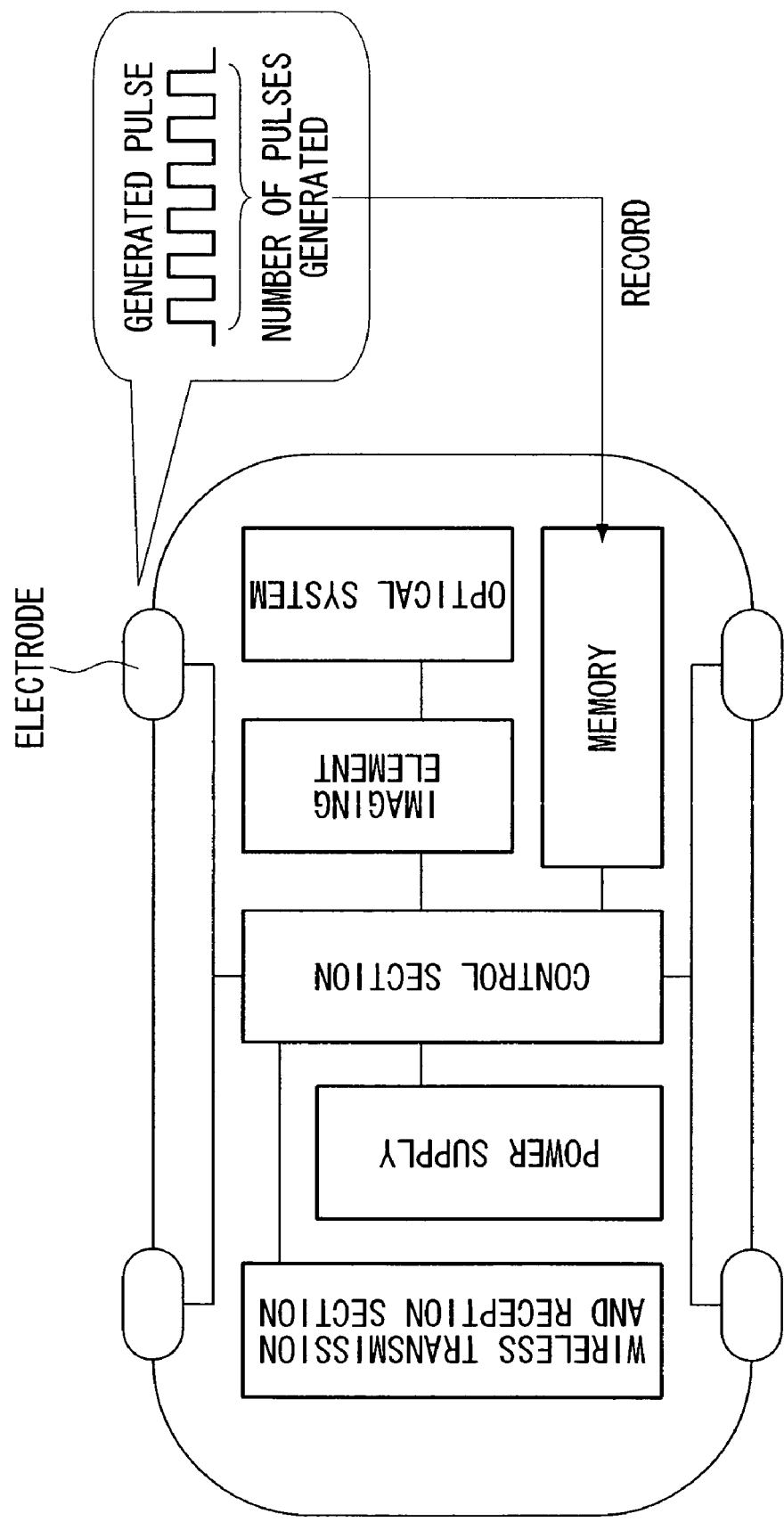
FIG. 36 is a sectional view showing yet another example of a capsule type medical device of the present invention.

It should be understood that the parameter is not limited to being a period of time; for example, as shown in FIG. 36, it would be acceptable for it to be the amount of electrical stimulation such as the number of pulses or the like which have been generated by the electrodes, and to make the decision as to the target site based upon the number of pulses. In this case, it would be acceptable to set the current generation circuit so as to supply electrical power in the form of pulses to the electrodes, to store the number of pulses which are generated in the memory, and to make the decision and to stop the generation of pulses and so on when this number has arrived at a number which is set in advance.

It should be understood that the amount of electrical stimulation may not only be the number of pulses; it would be acceptable for it to be the sum of the widths of the pulses, the distribution of the pulse strength, or the integrated value of the electric current which has been generated at the electrodes.

Furthermore, it would also be acceptable to utilize the features of any one, or of any combination, of the first variant example through the seventh variant example of the first embodiment, with the second embodiment.

Although, in the above, preferred embodiments of the present invention have been explained, the present invention is not to be considered as being limited to these embodiments described above. It would be possible to make various additions, omissions, substitutions, and other changes, within a range in which the gist of the present invention is not departed from. The present invention is not to be considered as being limited by the preceding explanations; rather, it should be limited only by the range of the appended claims.

What is claimed is:

1. A capsule type medical device system which comprises a capsule type medical device which can be ingested to within the living body, further comprising:
   a region determination device which determines a bodily region at which the capsule type medical device is located based on referencing information set in advance;
   an electrode which is provided on the capsule type medical device, and which applies an electrical stimulus to living body tissue; and
   a control device which is provided on the capsule type medical device, and which controls an electric current which flows to the electrode based on information of the bodily region determined by the region determination device;
   a second detection device which is provided on the capsule type medical device, and which detects in-vivo information within the living body;
   wherein the region determination device determines the bodily region at which the capsule type medical device is located by comparing the in-vivo information detected by the second detection device with the referencing information set in advance;
   wherein the second detection device comprises an acquisition device which acquires the in-vivo information;
   wherein the region determination device determines an orientation of the capsule type medical device within the body based on the in-vivo information which is acquired by the acquisition device; and
   wherein the control device controls the electric current which flows in the electrode based on the orientation of the capsule type medical device.

2. A capsule type medical device system according to claim 1, further comprising:
   a storage device which stores the in-vivo information.

3. A capsule type medical device system according to claim 1, further comprising:
   an electrical stimulation device which comprises a plurality of the electrodes;
   an electrode selection device which selects an electrode from among the plurality of electrodes, to apply an electrical stimulus;
   a contact detection device which electrically detects that the electrode is in contact with the living body tissue; and
   a control section which controls the electrical stimulation device, electrode selection device, and contact detection device.

4. A capsule type medical device system according to claim 3, wherein
   the electrical stimulation device comprises:
      one electrodes which are connected to the high electrical potential side, and
      the other electrodes which are connected to the low electrical potential side,
   the electrode selection device comprises:
      a first switching device which selects at least one electrode from among the one electrodes and connects it electrically to a supply source of electrical current; and
      a second switching device which selects at least one electrode from among the other electrodes.

5. A capsule type medical device system according to claim 4, wherein the one electrode and the other electrode are each disposed at equal intervals around the outer periphery of a cross section which is roughly orthogonal to an axial line which extends along the longitudinal direction of the casing of the capsule type medical device.

6. A capsule type medical device system according to claim 4, wherein the one electrode and the other electrode are disposed in multiple steps along the outer surface of the casing of the capsule type medical device, between from one end of the casing in its longitudinal direction to the other end thereof.

7. A capsule type medical device system according to claim 6, wherein
a projecting portion which includes an inclined portion which slopes with respect to the axial line along the longitudinal direction of the casing of the capsule type medical device is provided, and
the one electrode and the other electrode are provided upon the inclined surface.

8. A capsule type medical device system according to claim 7, wherein
the inclined portion comprises a portion which inclines towards a one end of the longitudinal direction of the casing of the capsule type medical device, and a portion which inclines towards the other end of the longitudinal direction of the casing, and
at least one group of the one electrode and the other electrode are disposed in respective portions of the inclined portion.

9. A capsule type medical device system according to claim 3, wherein the contact detection device is a force detection device.

10. A capsule type medical device system according to claim 9, wherein the force detection device is strain gauges which are equipped to the electrodes which are connected to the high electrical potential side and the electrodes which are connected to the low electrical potential side.

11. A capsule type medical device system according to claim 3, wherein the contact detection device is a device which measures the impedance between the electrode which is connected to the high electrical potential side and the electrode which is connected to the low electrical potential side.

12. A capsule type medical device system according to claim 3, wherein the electrical stimulation device comprises:
a waveform generator which generates a predetermined voltage waveform;
a conversion circuit which converts the voltage waveform to electric current;
a limitation circuit which is used for adjusting the electric current which flows to the electrode; and
an electric current sensor which detects the electric current, wherein the control section adjusts the gain of the limitation circuit according to the output of the electric current sensor.

13. A capsule type medical device system according to claim 12, wherein the electrical stimulation device comprises a resistor between the limitation circuit and the electrode.

14. A capsule type medical device system according to claim 12, wherein the electrical stimulation device generates an electric current waveform which is a continuous curve of roughly square form.

15. A capsule type medical device system according to claim 12, wherein the electrical stimulation device generates an electric current waveform which is a step shaped triangular wave.

16. The capsule type medical device system according to claim 1, further comprising a first detection device which detects positional information regarding a position at which the capsule type medical device is located, wherein
the region determination device determines the bodily region at which the capsule type medical device is located by comparing the positional information detected by the first detection device with the referencing information set in advance.

17. The capsule type medical device system according to claim 1, wherein
the second detection device comprises an acquisition device which acquires the in-vivo information, and
the region determination device determines the position of the capsule type medical device within the living body, by using the in-vivo information which is acquired by the acquisition device.

18. The capsule type medical device system according to claim 17, wherein
the acquisition device is an imaging device which takes images of the inside of the living body, and
the region determination device determines the position of the capsule type medical device within the living body, based upon an image which is taken by the imaging device.

19. The capsule type medical device system according to claim 18, wherein
the region determination device compares at least one characteristic of brightness, color, frequency distribution and bodily surface condition in the image with the referencing information set in advance, and thereby the region determination device determines the bodily region at which the capsule type medical device is located.

20. The capsule type medical device system according to claim 1, wherein
the capsule type medical device comprises a balloon which can be expanded so as to closely contact to living body tissue or can be shrunk down,
the electrode is provided upon the outer surface of the balloon, and
the control device expands or shrinks down the balloon, based upon the information of the bodily region.

21. The capsule type medical device system according to claim 17, wherein
the acquisition device is a pH sensor which measures the pH value within the living body, and
the region determination device determines the position of the capsule type medical device within the living body, based upon the pH value.

22. The capsule type medical device system according to claim 1, wherein
the capsule type medical device is provided with a plurality of the electrodes, and
the control device controls the electric current which flows in the plurality of electrodes, based upon the information of the bodily region.

23. The capsule type medical device system according to claim 1, further comprising
at least one of a body sampling section which samples the living body tissue and a body treatment section which treats the living body.

24. The capsule type medical device system according to claim 1, wherein
the electrode forms part of an outer surface of the capsule type medical device.

25. An operating method of capsule type medical device, comprising:
determining a bodily region at which the capsule type medical device is located based on referencing information set in advance;
generating a control signal based on information of the bodily region, controlling the electric current which flows to an electrode provided on the capsule type medical device using the generated control signal;

detecting in-vivo information within the living body with a second detection device which is provided on the capsule type medical device, wherein the second detection device comprises an acquisition device which acquires the in-vivo information;

wherein the determining of the bodily region at which the capsule type medical device is located comprises comparing the in-vivo information detected by the second detection device with the referencing information set in advance;

determining an orientation of the capsule type medical device within the body based on the in-vivo information which is acquired by the acquisition device; and wherein the controlling comprises controlling the electric current which flows in the electrode based on the orientation of the capsule type medical device.

26. The operating method of capsule type medical device according to claim 25, wherein the in-vivo information comprises at least one characteristic of brightness, color, frequency distribution and surface condition of the body.

27. An operating method of capsule type medical device, comprising:

determining a bodily region at which the capsule type medical device is located based on referencing information set in advance;

generating a control signal based on information of the bodily region, controlling the electric current which flows to an electrode provided on the capsule type medical device using the generated control signal;

detecting in-vivo information within the living body by acquiring the in-vivo information;

wherein the determining of the bodily region at which the capsule type medical device is located comprises comparing the acquired in-vivo information with the referencing information set in advance;

determining an orientation of the capsule type medical device within the body based on the acquired in-vivo information; and wherein the controlling comprises controlling the electric current which flows in the electrode based on the orientation of the capsule type medical device.

28. The operating method of capsule type medical device according to claim 27, wherein the in-vivo information comprises at least one characteristic of brightness, color, frequency distribution and surface condition of the body.

* * * * *